US012357958B2

(12) United States Patent
Fernandez Prieto et al.

(10) Patent No.: US 12,357,958 B2
(45) Date of Patent: Jul. 15, 2025

(54) CONSUMER PRODUCT COMPRISING BIODEGRADABLE DELIVERY PARTICLES

(71) Applicant: The Procter & Gamble Company, Cincinnati, OH (US)

(72) Inventors: Susana Fernandez Prieto, Benicarlo (ES); Valerie Francine Hans Eykens, Diest (BE); Timothy Roy Nijakowski, Mason, OH (US); Rita Del Pezzo, Brussels (BE); Johan Smets, Lubbeek (BE); Linsheng Feng, Menasha, WI (US); Travis Ian Bardsley, Appleton, WI (US); Fadi Selim Chakar, Neenah, WI (US); Robert Stanley Bobnock, Menasha, WI (US)

(73) Assignee: The Procter & Gamble Company, Cincinnati, OH (US)

( * ) Notice: Subject to any disclaimer, the term of this patent is extended or adjusted under 35 U.S.C. 154(b) by 803 days.

(21) Appl. No.: 17/529,310

(22) Filed: Nov. 18, 2021

(65) Prior Publication Data

US 2022/0152572 A1 May 19, 2022

Related U.S. Application Data

(60) Provisional application No. 63/115,786, filed on Nov. 19, 2020.

(51) Int. Cl.
| | | |
|---|---|---|
| *B01J 13/16* | (2006.01) | |
| *C08F 2/32* | (2006.01) | |
| *C08F 220/28* | (2006.01) | |
| *C08L 5/08* | (2006.01) | |

(52) U.S. Cl.
CPC ............. *B01J 13/16* (2013.01); *C08F 2/32* (2013.01); *C08F 220/286* (2020.02); *C08L 5/08* (2013.01); *C08F 2438/00* (2013.01); *C08L 2201/06* (2013.01); *C08L 2207/53* (2013.01)

(58) Field of Classification Search
CPC ......... B01J 13/16; C08F 2/32; C08F 220/286; C08F 2438/00; C08L 5/08; C08L 2201/06; C08L 2207/53
See application file for complete search history.

(56) References Cited

U.S. PATENT DOCUMENTS

| | | | |
|---|---|---|---|
| 5,573,934 A | 11/1996 | Hossainy et al. | |
| 7,932,191 B2 | 4/2011 | Dungworth et al. | |
| 8,466,232 B2 | 6/2013 | Berthier et al. | |
| 8,980,292 B2 | 3/2015 | Dihora et al. | |
| 9,561,169 B2 | 2/2017 | Dihora | |
| 9,714,397 B2 | 7/2017 | Feng et al. | |
| 9,999,579 B2 | 6/2018 | Feng | |
| 10,415,000 B2 | 9/2019 | Feng et al. | |
| 10,456,766 B2 | 10/2019 | Feng et al. | |
| 2010/0029539 A1 | 2/2010 | Dihora | |
| 2014/0079747 A1 | 3/2014 | Dihora | |
| 2014/0331896 A1 | 11/2014 | Heinzman | |
| 2016/0206522 A1 | 7/2016 | Ribaut et al. | |
| 2016/0256364 A1 | 9/2016 | Dihora et al. | |
| 2017/0002302 A1 | 1/2017 | Dihora | |
| 2018/0064615 A1 | 3/2018 | Brahms et al. | |
| 2018/0110250 A1 | 4/2018 | Popplewell | |
| 2018/0265818 A1 | 9/2018 | Smets | |
| 2019/0270064 A1 | 9/2019 | Postma | |
| 2020/0002653 A1 | 1/2020 | Smets | |
| 2020/0046628 A1 | 2/2020 | Jones et al. | |
| 2020/0056126 A1 | 2/2020 | Smets | |
| 2020/0122110 A1 | 4/2020 | Zhang et al. | |
| 2020/0222873 A1 | 7/2020 | Neuman et al. | |
| 2020/0360889 A1 | 11/2020 | Ortais et al. | |
| 2022/0119741 A1 | 4/2022 | Smets et al. | |
| 2022/0119742 A1 | 4/2022 | Smets et al. | |
| 2022/0396750 A1 | 12/2022 | Smets et al. | |
| 2023/0036889 A1 | 2/2023 | Struillou | |
| 2023/0120922 A1 | 4/2023 | Smets et al. | |
| 2024/0002745 A1 | 1/2024 | Fernández Prieto | |

FOREIGN PATENT DOCUMENTS

WO WO-2020131866 A1 * 6/2020 ............... A61K 8/11

OTHER PUBLICATIONS

All Office Actions; U.S. Appl. No. 17/529,308, filed Nov. 18, 2021.
All Office Actions; U.S. Appl. No. 17/529,312, filed Nov. 18, 2021.
Jyothi et al, "Microencapsulation techniques, factors influencing encapsulation efficiency", Journal of Microencapsulation, 27:3, pp. 187-197.
Thompson et al., "Colloidosomes: Synthesis, properties and applications", Journal of Colloid and Interface Science, 447, 2015, pp. 217-228.
U.S. Appl. No. 17/529,308, filed Nov. 18, 2021, to first inventor Susana Fernandez Prieto et al.
U.S. Appl. No. 17/529,312, filed Nov. 18, 2021, to first inventor Susana Fernandez Prieto et al.
15930 PCT Search Report and Written Opinion for PCT/US2021/059806 dated Feb. 22, 2022, 15 pages.

* cited by examiner

*Primary Examiner* — Ling Siu Choi
*Assistant Examiner* — Andrea Wu
(74) *Attorney, Agent, or Firm* — Kathleen Y. Carter

(57) ABSTRACT

A consumer product comprising a biodegradable delivery particle having a benefit agent containing core and a shell.

24 Claims, No Drawings

CONSUMER PRODUCT COMPRISING BIODEGRADABLE DELIVERY PARTICLES

FIELD OF THE INVENTION

The invention relates to consumer products comprising biodegradable delivery particles having a benefit agent containing core and a wall.

BACKGROUND OF THE INVENTION

Microencapsulation is a process where droplets of liquids, particles of solids or gasses are enclosed inside a solid shell and are generally in the micro-size range. The core material is then mechanically separated from the surrounding environment through a membrane (Jyothi et al., *Journal of Microencapsulation*, 2010, 27, 187-197). Microencapsulation technology is attracting attention from various fields of science and has a wide range of commercial applications for different industries. Overall, capsules are capable of one or more of (i) providing stability of a formulation or material via the mechanical separation of incompatible components, (ii) protecting the core material from the surrounding environment, (iii) masking or hiding an undesirable attribute of an active ingredient and (iv) controlling or triggering the release of the active ingredient to a specific time or location. All of these attributes can lead to an increase of the shelf-life of several products and a stabilization of the active ingredient in liquid formulations.

Encapsulation can be found in areas such as pharmaceuticals, personal care, textiles, food, coatings and agriculture. In addition, the main challenge faced by microencapsulation technologies in real-world commercial applications is that a complete retention of the encapsulated active within the capsule is required throughout the whole supply chain, until a controlled or triggered release of the core material is applied (Thompson et al., *Journal of Colloid and Interface Science*, 2015, 447, 217-228). There are significantly limited microencapsulation technologies that are safe for both the environment and human health with a long-term retention and active protection capability that can fulfill the needs of the industry nowadays, especially when it comes to encapsulation of small molecules.

Over the past several years, consumer goods manufacturers have used core-shell encapsulation techniques to preserve actives, such as benefit agents, in harsh environments and to release them at the desired time, which may be during or after use of the consumer goods. Among the several mechanisms that can be used for release of benefit agent, the one commonly relied upon is mechanical rupture of the capsule shell. Selection of mechanical rupture as the release mechanism constitutes another challenge to the manufacturer, as rupture must occur at specific desired times, even if the capsules are subject to mechanical stress prior to the desired release time.

Industrial interest for encapsulation technology has led to the development of several polymeric capsules chemistries which attempt to meet the requirements of biodegradability, low shell permeability, high deposition, targeted mechanical properties and rupture profile. Increased environmental concerns have put the polymeric capsules under scrutiny, therefore manufacturers have started investigating sustainable solutions for the encapsulation of benefit agents.

Biodegradable materials exist and are able to form delivery particles via coacervation, spray-drying or phase inversion precipitation. However, the delivery particles formed using these materials and techniques are highly porous and do not meet performance and stability specifications required for the containment and subsequent controlled release of the benefit agents.

Non-leaky and performing delivery particles in aqueous surfactant-based compositions exist, however due to its chemical nature and cross-linking, their biodegradability in aqueous environment is low.

Delivery particles are needed that are biodegradable, yet have structural integrity through inception, processing, storage, delivery, and final usage and resist damage from harsh environments.

SUMMARY OF THE INVENTION

A consumer product composition is provided that comprises a treatment adjunct and a population of delivery particles, wherein a delivery particle comprises a core and a wall encapsulating said core, wherein the core comprises a benefit agent and a partitioning modifier; the wall is formed by a radical polymerization reaction between: a) a water-soluble polysaccharide comprising at least one amine group; b) a multifunctional (meth)acrylate monomer and/or oligomer; c) optionally, a mono- and/or di-functional monomer and/or oligomer, d) at least one water-soluble thermal free radical initiator, e) at least one oil soluble thermal free radical initiator; wherein at least one of the water-soluble initiators is a persulfate and the water-soluble polysaccharide forms carbon/carbon, oxygen/carbon, and/or nitrogen/carbon bonds with the multifunctional (meth)acrylate monomer and/or oligomer, and with the proviso that the polysaccharide is not an amine ester modified starch.

DETAILED DESCRIPTION OF THE INVENTION

In accordance with embodiments, delivery particles with improved biodegradability comprising a core substantially enclosed in a polymer wall, the core comprising a benefit agent and a partitioning modifier, and the polymer wall obtained by the reaction of polymerizable monomers or oligomers, such as (meth)acrylate monomers, with polysaccharides comprising at least one amine group using at least one persulfate initiator to initiate the polymerization of the wall. Examples of polysaccharides comprising at least one amine group include chitosan and chitin.

The present invention includes novel delivery particles produced from cross-linking biodegradable polymers with smaller monomers in order to enhance the bioavailability of the wall and the biodegradability of the overall delivery particle. Without being bound by theory, it is believed that the biodegradable polysaccharides comprising at least one amine group form a network that enhances the accessibility of the enzymes during degradation process, while the small monomers close the delivery particle structure making it compacted enough to protect the benefit agent in an aqueous surfactant-based composition.

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to fine fragrances (e.g. perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, Rx pharmaceuticals, pet health and nutrition, and water purification.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various pouches, tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof. The form of such compositions includes liquids, gels, beads, powders, flakes, and granules.

As used herein, the phrase "benefit agent containing delivery particle" encompasses microcapsules including perfume microcapsules.

As used herein, the terms "delivery particle", "benefit agent containing delivery particle", "encapsulated benefit agent" "capsule" and "microcapsule" are synonymous.

As used herein, reference to the term "(meth)acrylate" or "(meth)acrylic" is to be understood as referring to both the acrylate and the methacrylate versions of the specified monomer, oligomer and/or prepolymer. (for example "allyl (meth)acrylate" indicates that both allyl methacrylate and allyl acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible).

For purposes of this application, the partitioning modifier is not considered a perfume raw material and thus it is not considered when calculating perfume compositions/formulations. Thus, the amount of partitioning modifier present is not used to make such calculations.

As used herein the term "water-soluble material" means a material that has a solubility of at least 0.5% wt in water at 60° C.

As used herein the term "oil soluble" means a material that has a solubility of at least 0.1% wt in the core of interest at 50° C.

As used herein the term "oil dispersible" means a material that can be dispersed at least 0.1% wt in the core of interest at 50° C. without visible agglomerates.

As used herein, the articles including "a" and "an" when used in a claim, are understood to mean one or more of what is claimed or described.

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the terms "site" or "site of attachment" or "point of attachment" all mean an atom (e.g. A) having an open valence within a chemical group or defined structural entity that is designated with a symbol (*-A) to indicate that the so-designated atom A connects to another atom in a separate chemical group via a covalent chemical bond.

As used herein "biodegradable" refers to a material that has above 30% $CO_2$ release according to the OECD301B test method.

Consumer Product Composition

The present disclosure relates to a consumer product composition that comprises a population of delivery particles and a treatment adjunct as described in more detail below.

Delivery Particle

The consumer product composition of the present invention comprises a delivery particle comprising a core and a wall encapsulating said core.

The wall is formed by a radical polymerization reaction between:
  a) a water-soluble polysaccharide comprising at least one amine group, with the proviso that the polysaccharide is not an amine ester modified starch.
  b) a multifunctional (meth)acrylate monomer and/or oligomer,
  c) optionally, a mono- and/or di-functional monomer and/or oligomer,
  d) at least one water-soluble thermal free radical initiator,
  e) at least one oil soluble thermal free radical initiator;
wherein at least one of the water-soluble initiators is a persulfate and the water-soluble polysaccharide forms carbon/carbon, oxygen/carbon, and/or nitrogen/carbon bonds with the multifunctional (meth)acrylate monomer and/or oligomer. In preferred embodiments, the water-soluble polysaccharide forms carbon/carbon bonds with the multifunctional (meth)acrylate monomer and/or oligomer.

In embodiments, the water-soluble polysaccharide may comprise at least one primary amine.

In embodiments, the water-soluble polysaccharide may further comprise hydroxyl moieties. In embodiments, the water-soluble polysaccharide is selected from the group consisting of chitosan, chitin or mixtures thereof.

In embodiments, the water-soluble polysaccharide is chitosan or chitin, and preferably with a degree of deacetylation ("DDA") of at least 50%, preferably at least 65% and more preferably at least 75%. In embodiments, the chitosan has a weight average molecular weight from about 30 kDa to about 500 kDa, preferably from about 50 kDa to about 300 kDa, even more preferably from about 80 kDa to about 200 kDa.

In embodiments, the water-soluble polysaccharide may be from about 2% to about 95%, preferably at least 5%, even more preferably at least 10% weight percentage of the total wall weight. In embodiments, the water-soluble polysaccharide may be from about 10% to about 75% weight percentage of the total wall weight.

In embodiments, the wall further comprises a polymer comprising hydroxyl moieties. In embodiments, the polymer comprising hydroxyl moieties is selected from the group consisting of pectin, carrageenan, cellulose, xanthan gum, tara gum, konjac gum, alginate, hyaluronic acid, amylose, lignin, diutan gum, gelatin, poly(vinyl alcohol) and mixtures thereof, preferably poly(vinyl alcohol).

In embodiments, the polymer comprising hydroxyl moieties is poly(vinyl alcohol) with a weight average molecular weight from about 30 kDa to about 500 kDa, preferably from about 50 kDa to about 300 kDa, even more preferably from about 80 kDa to about 200 kDa. The poly(vinyl alcohol) preferably has a hydrolysis degree from about 55% to about 99%, preferably from about 75% to about 95%, more preferably from about 85% to about 90%, and most preferably from about 87% to about 89%.

In embodiments, the polymer comprising hydroxyl moieties may be from about 10% to about 93%, preferably at least 25%, even more preferably at least 50% weight percentage of the total wall weight.

In embodiments, the water-soluble polysaccharide and/or the polymer comprising hydroxyl moieties has a molecular weight from about 30 kDa to about 500 kDa, preferably from about 50 kDa to about 300 kDa, even more preferably from about 80 kDa to about 200 kDa.

In embodiments, the water-soluble polysaccharide and/or the polymer has a biodegradability in 60 days following OECD 301B test from about 30% to about 100% $CO_2$, preferably above 40% $CO_2$, more preferably above 50% $CO_2$, even more preferably above 60% $CO_2$.

In embodiments, the polymer wall further comprises at least one multi-functional (meth)acrylate monomer and/or oligomer. In embodiments, the one or more oil-soluble or oil-dispersible multifunctional monomers or oligomers may comprise at least two radical polymerizable functional groups, preferably at least three radical polymerizable functional groups, preferably at least four radical polymerizable functional groups, more preferably at least five radical polymerizable functional groups, even more preferably at least six radical polymerizable functional groups. In embodiments, the one or more oil-soluble or oil-dispersible multifunctional (meth)acrylate monomers or oligomers may comprise more than six radical polymerizable functional groups. It is believed that monomers comprising a relatively greater number of radical polymerizable functional groups result in, for example, delivery particles with more compact walls and having preferred properties, such as less leakage, compared to walls formed from monomers that have fewer radical polymerizable functional groups.

In embodiments, at least two of the radical polymerizable functional groups, or at least three of the radical polymerizable functional groups, or at least four of the radical polymerizable functional groups, or at least five of the radical polymerizable functional groups, or at least six of the radical polymerizable functional groups are an acrylate or methacrylate group. Preferably, the radical polymerizable functional groups are each independently selected from the group consisting of acrylate and methacrylate. In embodiments, the radical polymerizable functional groups of the multi-functional monomer and/or oligomer are all the same. It is believed that these radical polymerizable functional groups result in delivery particles having preferred properties, such as less leakage at high core:wall ratios, compared to other functional groups. In embodiments delivery particles may have leakage values of below about 50% or below about 30%, as determined by the Leakage Test described in the TEST METHODS Section.

The oil-soluble or oil-dispersible multifunctional (meth)acrylate monomers or oligomers may comprise a multifunctional aromatic urethane acrylate. Preferably, the oil-soluble or oil-dispersible multifunctional (meth)acrylate monomers or oligomers comprises a hexafunctional aromatic urethane acrylate.

In embodiments, the multifunctional (meth)acrylate monomer and/or oligomer may be from about 5% to about 50%, preferably at least 10%, even more preferably at least 20% weight percentage of the total wall weight.

Additionally or alternatively, the oil-soluble or oil-dispersible multifunctional (meth)acrylate monomers or oligomers may comprise a multifunctional aliphatic urethane acrylate.

The wall may be formed from at least two different multifunctional (meth)acrylate monomers, for example first and second multifunctional (meth)acrylate monomers. The first multifunctional (meth)acrylate monomer may comprise a different number of radical polymerizable functional groups compared to the second multifunctional (meth)acrylate monomer. For example, the first multifunctional (meth) acrylate monomer may comprise six (meth)acrylate groups (e.g., hexafunctional), and the second multifunctional (meth)acrylate monomer may comprise less than six (meth) acrylate groups, such as a number selected from two (e.g., difunctional), three (e.g., trifunctional), four (e.g., tetrafunctional), or five (e.g., pentafunctional), preferably five. In embodiments, the first and second multifunctional (meth) acrylate monomers may comprise the same number of radical polymerizable functional groups, such as six (e.g., both monomers are hexafunctional), although the respective monomers are characterized by different structures or chemistries. In embodiments, the first and second multifunctional (meth)acrylate monomers may comprise different number of radical polymerizable functional groups, such as six and two.

In addition to the oil-soluble or oil-dispersible multifunctional (meth)acrylate monomer or oligomer, the wall may be further formed by a water-soluble or water-dispersible multifunctional (meth)acrylate monomer or oligomer, which may include a hydrophilic functional group. The water-soluble or water-dispersible multifunctional (meth) acrylate monomer or oligomer may be preferably selected from the group consisting of polyethylene glycol di(meth)acrylates, ethoxylated multi-functional (meth)acrylates, and mixtures thereof, for example trimethylolpropane tri(meth)acrylate, ethylene glycol di(meth)acrylate, di-, tri- and tetraethyleneglycol di(meth)acrylate, dipropylene glycol di(meth)acrylate, polyethylene glycol di(meth)acrylate, di(pentamethylene glycol) di(meth)acrylate, ethylene di(meth)acrylate, neopentyl glycol di(meth)acrylate, trimethylolpropane tri(meth)acrylate, diglycerol di(meth)acrylate, neopentyl di(meth)acrylate, trimethylolpropane tri(meth)acrylate, polyethylene glycol di(meth)acrylate and dipropylene glycol di(meth)acrylate and mixtures thereof. Such water-soluble or water-dispersible multifunctional (meth)acrylate monomer or oligomer may be added to the oil phase, to the water phase or to both of them during encapsulation process.

In embodiments, the mono- and/or di-functional monomer and/or oligomer may be independently selected from the group consisting of:

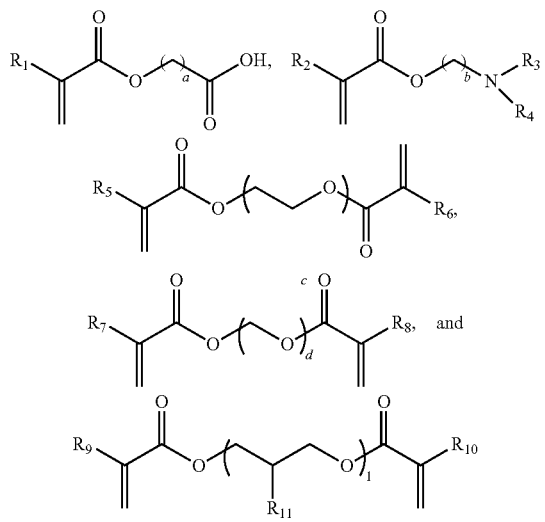

wherein
$R_1$, $R_2$, $R_5$, $R_6$, $R_7$, $R_8$, $R_9$ and $R_{10}$ are independently selected from the group consisting of a hydrogen (*—H) and a methyl group (*—$CH_3$);
a, b, c and d are integers independently selected from 1 to 10, preferably from 2 to 5,
$R_3$ and $R_4$ are independently selected from the group consisting of

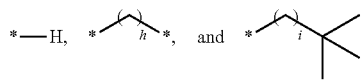

h and i are integers independently selected from 0 to 10, preferably from 1 to 5;
$R_{11}$ is selected from the group consisting of hydroxyl (*—OH), hydrogen (*—H), and methyl group (*—$CH_3$).

In embodiments, the wall may further comprise a monomer selected from an amine (meth)acrylate, an acidic (meth)acrylate, or a combination thereof.

Suitable amine (meth)acrylates for use in the particles of the present disclosure may include aminoalkyl acrylate or aminoalkyl methacrylate including, for example, but not by way of limitation, ethylaminoethyl acrylate, ethylaminoethyl methacrylate, aminoethyl acrylate, aminoethyl methacrylate, tertiarybutyl aminoethyl acrylate, tertiarybutyl aminoethyl methacrylate, diethylamino acrylate, diethylamino methacrylate, diethylaminoethyl acrylate, diethylaminoethyl methacrylate, dimethylaminoethyl acrylate and dimethylaminoethyl methacrylate. Preferably, the amine (meth)acrylate is aminoethyl acrylate or aminoethyl methacrylate, or tertiarybutyl aminoethyl methacrylate.

Suitable carboxy (meth)acrylates for use in particles of the present disclosure may include 2-carboxyethyl acrylate, 2-carboxyethyl methacrylate, 2-carboxypropyl acrylate, 2-carboxypropyl methacrylate, carboxyoctyl acrylate, carboxyoctyl methacrylate. Carboxy substituted aryl acrylates or methacrylates may include 2-acryloyloxybenzoic acid, 3-acryloyloxybenzoic acid, 4-acryloyloxybenzoic acid, 2-methacryloyloxybenzoic acid, 3-methacryloyloxybenzoic acid, and 4-methacryloyloxybenzoic acid. (Meth)acryloyloxyphenylalkylcarboxy acids by way of illustration and not limitation can include 4-acryloyloxyphenylacetic acid or 4-methacryloyloxyphenylacetic acid.

In embodiments, the wall may be further derived, at least in part, from at least one free radical initiator, preferably at least two free radical initiators, even more preferably at least three radical initiators. In embodiments, at least one free radical initiator may preferably comprise a water-soluble or water-dispersible free radical initiator. In embodiments, at least one free radical initiator may preferably comprise an oil-soluble or oil-dispersible free radical initiator. In a preferred embodiment, the wall may be formed, at least in part, from the combination of at least one water-soluble or water-dispersible free radical initiator and at least one oil-soluble or oil-dispersible free radical initiator. In embodiments, the wall is derived, at least in part, from a persulfate initiator selected from the group consisting of ammonium persulfate, sodium persulfate, potassium persulfate and mixtures thereof. Preferably, the persulfate initiator is potassium persulfate.

Without wishing to be bound by theory, it is believed that selecting the appropriate amount of initiator relative to total wall material (and/or wall monomers/oligomers) can result in improved capsules. For example, it is believed that levels of initiators that are too low may lead to poor polymer wall formation; levels that are too high may lead to encapsulate walls that have relatively low levels of structural monomers. In either situation, the resulting capsules may be relatively leaky and/or weak.

Thus, the amount of initiator present may be from about 0.1% to about 30%, preferably from about 0.5% to about 25%, more preferably from about 0.8% to about 15%, even more preferably from about 1% to about 10%, even more preferably from about 1% to about 8%, by weight of the wall. It is believed that relatively higher amounts of initiator within the disclosed ranges may lead to improved, less-leaky capsules. The optimal amount of initiator may vary according to the nature of the core material. The polymer wall may be derived from a first initiator and a second initiator, wherein the first and second initiators are present in a weight ratio of from about 5:1 to about 1:5, or preferably from about 3:1 to about 1:3, or more preferably from about 2:1 to about 1:2, or even more preferably from about 1.5:1 to about 1:1.5.

Suitable free radical initiators may include azo initiators. More particularly, and without limitation, the free radical initiator can be selected from the group consisting of 2,2'-azobis(isobutylnitrile), 2,2'-azobis(2,4-dimethylpentanenitrile), 2,2'-azobis (2,4-dimethylvaleronitrile), 2,2'-azobis(2-methylpropanenitrile), 2,2'-azobis(2-methylbutyronitrile), 1,1'-azobis (cyclohexanecarbonitrile), 1,1'-azobis(cyanocyclohexane), and mixtures thereof.

In embodiments, the water-soluble comprising at least one amine group and/or polymer may be fragmented by the water-soluble initiator prior to form carbon/carbon, nitrogen/carbon and/or oxygen/carbon bonds with the multifunctional (meth)acrylate monomer and/or oligomer.

The delivery particles of the present disclosure include a core. The core may comprise a benefit agent. Suitable benefit agents located in the core may include benefit agents that provide benefits to a surface, such as a fabric or hair.

The core may comprise from about 40% to about 95%, preferably from about 50% to about 80%, more preferably from about 50% to about 70%, by weight of the core, of the benefit agent.

The benefit agent may be selected from the group consisting of fragrance, silicone oils, waxes, hydrocarbons, higher fatty acids, essential oils, lubricants, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, skin care agents, glycerin, synthetic or natural actives, antibacterial actives, antiperspirant actives, cationic polymers, dyes, and mixtures thereof. Preferably the benefit agent comprises fragrance, essential oils and mixtures thereof.

The encapsulated benefit agent may preferably a fragrance, which may include one or more perfume raw materials. The term "perfume raw material" (or "PRM") as used herein refers to compounds having a molecular weight of at least about 100 g/mol and which are useful in imparting an odor, fragrance, essence or scent, either alone or with other perfume raw materials. Typical PRMs comprise inter alia alcohols, ketones, aldehydes, esters, ethers, nitriles and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

The PRMs may be characterized by their boiling points (B.P.) measured at the normal pressure (760 mm Hg), and their octanol/water partitioning coefficient (P), which may be described in terms of log P, determined according to the test method below. Based on these characteristics, the PRMs may be categorized as Quadrant I, Quadrant II, Quadrant III, or Quadrant IV perfumes, as described in more detail below.

The fragrance may comprise perfume raw materials that have a log P of from about 2.5 to about 4. It is understood that other perfume raw materials may also be present in the fragrance.

The perfume raw materials may comprise a perfume raw material selected from the group consisting of perfume raw materials having a boiling point (B.P.) lower than about 250° C. and a log P lower than about 3, perfume raw materials having a B.P. of greater than about 250° C. and a log P of greater than about 3, perfume raw materials having a B.P. of greater than about 250° C. and a log P lower than about 3, perfume raw materials having a B.P. lower than about 250° C. and a log P greater than about 3 and mixtures thereof. Perfume raw materials having a boiling point B.P. lower than about 250° C. and a log P lower than about 3 are known as Quadrant I perfume raw materials. Quadrant I perfume raw materials are preferably limited to less than 30% of the perfume composition. Perfume raw materials having a B.P. of greater than about 250° C. and a log P of greater than about 3 are known as Quadrant IV perfume raw materials, perfume raw materials having a B.P. of greater than about 250° C. and a log P lower than about 3 are known as Quadrant II perfume raw materials, perfume raw materials having a B.P. lower than about 250° C. and a log P greater than about 3 are known as a Quadrant III perfume raw materials. Suitable Quadrant I, II, III and IV perfume raw materials are disclosed in U.S. Pat. No. 6,869,923 B1.

The core of the delivery particles of the present disclosure may further comprise a partitioning modifier. The properties of the partitioning modifier in the core can play a role in determining how much, how quickly, and/or how permeable the polyacrylate shell material will be when established at the oil/water interface. For example, if the oil phase comprises highly polar materials, these materials may reduce the diffusion of the acrylate oligomers and polymers to the oil/water interface and result in a very thin, highly permeable shell. Incorporation of a partitioning modifier can adjust the polarity of the core, thereby changing the partition coefficient of the polar materials in the partitioning modifier versus the acrylate oligomers, and can result in the establishment of a well-defined, highly impermeable shell. The partitioning modifier may be combined with the core's benefit agent prior to incorporation of the wall-forming monomers.

The partitioning modifier may be present in the core at a level of from about 5% to about 60%, preferably from about 20% to about 50%, more preferably from about 30% to about 50%, by weight of the core.

The partitioning modifier may comprise a material selected from the group consisting of vegetable oil, modified vegetable oil, mono-, di-, and tri-esters of $C_4$-$C_{24}$ fatty acids, isopropyl myristate, dodecanophenone, lauryl laurate, methyl behenate, methyl laurate, methyl palmitate, methyl stearate, and mixtures thereof. The partitioning modifier may preferably comprise or even consist of isopropyl myristate. The modified vegetable oil may be esterified and/or brominated. The modified vegetable oil may preferably comprise castor oil and/or soybean oil. US Patent Application Publication 20110268802, incorporated herein by reference, describes other partitioning modifiers that may be useful in the presently described delivery particles.

Delivery particles may be made according to known methods. Methods may be further adjusted to achieve desired characteristics described herein, such as volume-weighted particle size, relative amounts of benefit agent and/or partitioning modifier, etc.

For example, the present disclosure relates to a process of making a population of delivery particles comprising a core and a polymer wall encapsulating the core. The process may comprise the step of providing an oil phase. The oil phase may comprise a benefit agent and a partition modifier, as described above. The process may further comprise dissolving or dispersing into the oil phase one or more multifunctional (meth)acrylate monomers or oligomers having at least two radical polymerizable functional groups, and preferably at least three radical polymerizable functional groups, at least four radical polymerizable functional groups, at least five radical polymerizable functional groups, or even at least six radical polymerizable functional groups.

The multifunctional monomers or oligomers are described in more detail above. Among other things, the multifunctional monomers or oligomers may comprise a multifunctional aromatic urethane acrylate, preferably a tri-, tetra-, penta-, or hexafunctional aromatic urethane acrylate, or mixtures thereof, preferably comprising a hexafunctional aromatic urethane acrylate. The monomer or oligomer may comprise one or more multifunctional aliphatic urethane acrylates, which may be dissolved or dispersed into the oil phase. The process may further comprise dissolving or dispersing one or more of an amine (meth)acrylate or an acidic (meth)acrylate into the oil phase.

The process further comprises a water phase comprising a water-soluble polysaccharide comprising at least one amine group (described above) and a persulfate initiator.

The water phase may further comprise a polymer comprising hydroxyl moieties (described above) an emulsifier, a surfactant, or a combination thereof. Preferably the pH from the water phase is adjusted from 3 to 7, more preferably from 4 to 6, and even more preferably at 4.5. The process may further comprise the step of dissolving or dispersing into the water phase one or more water-soluble or water-dispersible mono- or multi-functional (meth)acrylate monomers and/or oligomers.

The process may comprising a step of dissolving or dispersing into the water phase, the oil phases, or both, one or more amine (meth)acrylates, acidic (meth)acrylates, polyethylene glycol di(meth)acrylates, ethoxylated mono- or multi-functional (meth)acrylates, and/or other (meth)acrylate monomers and/or oligomers.

In general, the oil soluble multifunctional monomer is soluble or dispersible in the oil phase, typically soluble at least to the extent of 0.1 grams in 100 ml of the oil, or dispersible or emulsifiable therein at 50° C. The water-soluble multifunctional monomers are typically soluble or dispersible in water, typically soluble at least to the extent of 1 gram in 100 ml of water, or dispersible therein at 22° C.

Typically, the oil phase is combined with an excess of the water phase. If more than one oil phase is employed, these generally are first combined, and then combined with the water phase. If desired, the water phase can also comprise one or more water phases that are sequentially combined.

The oil phase may be emulsified into the water phase under high shear agitation to form an oil-in-water emulsion, which may comprise droplets of the core materials dispersed in the water phase. Typically, the amount of shear agitation applied can be controlled to form droplets of a target size, which influences the final size of the finished encapsulates.

The dissolved or dispersed monomers may be reacted by heating or actinic irradiation of the emulsion. The reaction can form a polymer wall at an interface of the droplets and the water phase. The radical polymerizable functional groups of the multifunctional monomer or oligomer, upon heating, facilitate self-polymerization.

One or more free radical initiators may be provided to the oil phase, the water phase, or both, preferably both. For example, the process may comprise adding one or more free radical initiators to the water phase, for example to provide a further source of free radicals upon activation by heat. The process may comprise adding one or more free radical initiators to the oil phase. The one or more free radical initiators may be added to the water phase, the oil phase, or both in an amount of from greater than 0% to about 5%, by weight of the respective phase. Latent initiators are also contemplated where a first action, particularly a chemical reaction, is needed to transform the latent initiator into an active initiator which subsequently initiates polymerization upon exposure to polymerizing conditions. Where multiple initiators are present, it is contemplated, and preferred, that each initiator be initiated or suitably initiated by a different condition.

Alternatively, the reacting step may be carried out in the absence of an initiator, as it has surprisingly been found that encapsulates may form, even when a free radical initiator is not present.

In the described process, the heating step may comprise heating the emulsion from about 1 hour to about 20 hours, preferably from about 2 hours to about 15 hours, more preferably about 4 hours to about 10 hours, most preferably from about 5 to about 7 hours, thereby heating sufficiently to transfer from about 500 joules/kg to about 5000 joules/kg to said emulsion, from about 1000 joules/kg to about 4500 joules/kg to said emulsion, from about 2900 joules/kg to about 4000 joules/kg to said emulsion.

Prior to the heating step, the emulsion may be characterized by a volume-weighted median particle size of the emulsion droplets of from about 0.5 microns to about 100 microns, even from about 1 microns to about 60 microns, or even from 20 to 50 microns, preferably from about 30 microns to about 50 microns, with a view to forming a population of delivery particles with a volume-weighted target size, for example, of from about 30 to about 50 microns.

The benefit agent may be selected as described above and is preferably a fragrance that comprises one or more perfume raw materials. The benefit agent may be the primary, or even only component, of the oil phase into which the other materials are dissolved or dispersed.

The partitioning modifier may be selected from the group consisting of isopropyl myristate, vegetable oil, modified vegetable oil, mono-, di-, and tri-esters of C4-C24 fatty acids, dodecanophenone, lauryl laurate, methyl behenate, methyl laurate, methyl palmitate, methyl stearate, and mixtures thereof, preferably isopropyl myristate. The partitioning modifier may be provided in an amount so as to comprise from about 5% to about 60% by weight of the core of the delivery particle.

As a result of the method of making delivery particles provided herein, the delivery particles may be present in an aqueous slurry, for example, the particles may be present in the slurry at a level of from about 10% to about 60%, preferably from about 20% to about 50%, by weight of the slurry. Additional materials may be added to the slurry, such as preservatives, solvents, structurants, or other processing or stability aids. The slurry may comprise one or more perfumes (i.e., unencapsulated perfumes) that are different from the perfume or perfumes contained in the core of the benefit agent delivery particles.

As discussed previously, an emulsion is formed by emulsifying under high shear agitation the oil or combined oils into the water phase. Optionally the water phase can also include emulsifiers. The water phase emulsifier can be selected form one or more of polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, or copolymers of polyvinyl alcohol polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene), pickering emulsifiers and mixtures thereof. Especially useful polyvinyl alcohols include polyvinyl alcohols of molecular 13,000 to 1,876,000 Daltons, preferably from 13,000 to about 230,000 Daltons, or even from 146,000 to 186,000 Daltons. The polyvinyl alcohol can be partially or fully hydrolyzed. Polyvinyl alcohol partially hydrolyzed in the range of 80 to 95% hydrolyzed is preferred, even more preferred 87% to 89% hydrolyzed. Especially useful pickering emulsifiers include hydrophobic or modified pickering emulsifiers with a surface area from about 90 to about 280 $m^2$ per gram, such as Aerosil® R-805 and R-816 from Evonik.

Optionally, deposition aids can be included, or applied as a coating in one or more layers over formed or forming delivery particles, to increase deposition or adhesion of the delivery particles to various surfaces such as various substrates including but not limited to paper, fabric skin, hair, towels, or other surfaces. Deposition aids can include poly (meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co-polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof. In a further embodiment, the above-described delivery particles can comprise a deposition aid, and in a further aspect the deposition aid coats the outer surface of the wall of the delivery particle.

Consumer Product Compositions

The present application discloses novel compositions, including novel consumer product compositions comprising benefit agent containing delivery particles comprising a core and a shell encapsulating the core.

The present application relates to processes for making any of the compositions described herein. The process of making a composition may comprise the step of combining a benefit agent delivery particle as described herein with an adjunct material which may be a consumer product adjunct material as described herein.

The particles may be combined with such one or more adjunct materials such as consumer product adjuncts materials when the particles are in one or more forms, including a slurry form, neat particle form, and/or spray dried particle form. The particles may be combined with adjunct materials such as consumer product adjuncts materials by methods that include mixing and/or spraying.

The compositions of the present disclosure can be formulated into any suitable form and prepared by any process chosen by the formulator. The particles and adjunct materials may be combined in a batch process, in a circulation loop process, and/or by an in-line mixing process. Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders.

Hair Care Compositions

The delivery particle of the current invention can be used in hair care compositions to provide one or more benefits, including freshness, malodor removal, softness and styling. The hair care compositions of the present invention can be in different forms. Non-limiting examples of said forms are shampoos, conditioning shampoos, pet shampoo, leave-on treatments, sprays, liquids, pastes, Newtonian or non-Newtonian fluids, gels, and sols.

The hair care composition preferably comprises delivery particles at least comprising one benefit agent at a level where upon directed use, promotes one or more benefits without detriment to the hair. Such benefit agent may comprise a perfume, an essential oil, a silicone, a wax and mixtures thereof. The perfume may comprise a single perfume raw material or a mixture of perfume raw materials. Examples of essential oils are argan oil, lavender oil, peppermint oil, rosemary oil, thyme oil, cedarwood oil, lemongrass oil, ylang-ylang oil and mixtures thereof.

In one embodiment of the present invention, said hair care composition comprises between about 0.01 wt % to about 15 wt % of at least one benefit agent encapsulated in a delivery particle. In another embodiment, said hair care composition comprises between about 0.05 wt % to about 8 wt % of at least one benefit agent encapsulated. In another embodiment, said hair care composition comprises between about 0.1 wt % to about 5 wt % of at least one benefit agent encapsulated.

In addition to at least one delivery particle, the hair care compositions of the present invention may also include detersive surfactants, aqueous carriers, shampoo gel matrixes, and other additional ingredients.

Detersive Surfactant

The hair care composition comprises one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the hair care composition should be sufficient to provide the desired cleaning and lather performance, and generally ranges from 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat.

Nos. 2,486,921; 2,486,922; and 2,396,278, which are incorporated herein by reference in their entirety.

Exemplary anionic surfactants for use in the hair care composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the hair care composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the hair care composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present hair care composition include cocoamphoacetate, cocoamphodiacetate, lauroamphoacetate, lauroamphodiacetate, and mixtures thereof.

Zwitterionic detersive surfactants suitable for use in the hair care composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the hair care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The hair care composition may also comprise a shampoo gel matrix, an aqueous carrier, and other additional ingredients described herein.

Aqueous Carrier

The hair care composition comprises a first aqueous carrier. The level and species of the carrier are selected according to the compatibility with other components, and other desired characteristic of the product. Accordingly, the formulations of the hair care composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

Shampoo Gel Matrix

In one embodiment, the hair care composition described herein may comprise a shampoo gel matrix. The shampoo gel matrix comprises (i) from about 0.1% to about 20% of one or more fatty alcohols, alternative from about 0.5% to about 14%, alternatively from about 1% to about 10%, alternatively from about 6% to about 8%, by weight of the shampoo gel matrix; (ii) from about 0.1% to about 10% of one or more shampoo gel matrix surfactants, by weight of the shampoo gel matrix; and (iii) from about 20% to about 95% of an aqueous carrier, alternatively from about 60% to about 85% by weight of the shampoo gel matrix.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Additional Ingredients

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the silicones can be in an emulsified form with droplet size of about 10 nm to about 30 micrometers Other solid or semisolid conditioning agents may be present in the composition including high melting temperature fatty alcohols, acids, esters, amides or oligomers from unsaturated esters, alcohols, amides. The oligomeric esters may be the result of oligomerization of naturally-occurring unsaturated glyceride esters. Such solid or semi-solid conditioning agents may be added or present as mixtures with organic oils.

Nonionic Polymers

The hair care composition of the present invention may also further comprise a nonionic polymer. According to an embodiment, the conditioning agent for use in the hair care composition of the present invention may include a polyalkylene glycol polymer. For example, polyalkylene glycols having a molecular weight of more than about 1000 are useful herein. Useful are those having the following general formula (VIII):

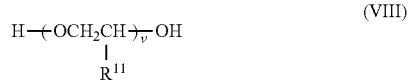
(VIII)

wherein $R^{11}$ is selected from the group consisting of H, methyl, and mixtures thereof; and v is the number of ethoxy units. The polyalkylene glycols, such as polyethylene glycols, can be included in the hair care compositions of the present invention at a level of from about 0.001 wt. % to about 10 wt. %. In an embodiment, the polyethylene glycol is present in an amount up to about 5 wt. % based on the weight of the composition. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

Organic Conditioning Materials

The conditioning agent of the compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Deposition Aids

The hair care compositions of the present invention may further comprise a deposition aid, such as a cationic polymer. Cationic polymers useful herein are those having an average molecular weight of at least about 5,000, alternatively from about 10,000 to about 10 million, and alternatively from about 100,000 to about 2 million.

Suitable cationic polymers include, for example, copolymers of vinyl monomers having cationic amine or quaternary ammonium functionalities with water-soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol (made by hydrolysis of polyvinyl acetate), maleic anhydride, propylene glycol, and ethylene glycol. Other suitable cationic polymers useful herein include, for example, cationic celluloses, cationic starches, and cationic guar gums.

The cationic polymer can be included in the hair care compositions of the present invention at a level of from about 0.001 wt. % to about 10 wt. %. In one embodiment, the cationic polymer is present in an amount up to about 5 wt % based on the weight of the composition.

Hair Care Benefit Agents

In an embodiment, the hair care composition further comprises one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, chelants, perfumes, brighteners, enzymes, sensates, attractants, dyes, pigments, bleaches, and mixtures thereof.

Rheology Modifier/Suspending Agents

In one embodiment, the rinse-off hair care composition comprises a rheology modifier. The rheology modifier increases the substantivity and stability of the composition, improves feel and consumer's use experience (e.g. non-dripping, spreadability, etc). Any suitable rheology modifier can be used. In an embodiment, the hair care composition may comprise from about 0.05% to about 10% of a rheology modifier, in a further embodiment, from about 0.1% to about 10% of a rheology modifier, in yet a further embodiment, from about 0.5% to about 2% of a rheology modifier, in a further embodiment, from about 0.7% to about 2% of a rheology modifier, and in a further embodiment from about 1% to about 1.5% of a rheology modifier. In an embodiment, the rheology modifier may be a polyacrylamide thickener. In an embodiment, the rheology modifier may be a polymeric rheology modifier.

In an embodiment, the composition of the present invention may comprise suspending agents including crystalline suspending agents which can be categorized as acyl derivatives, long chain amine oxides, and mixtures thereof. These suspending agents are described in U.S. Pat. No. 4,741,855. These suspending agents include ethylene glycol esters of fatty acids in one aspect having from about 16 to about 22 carbon atoms. In embodiments, useful suspending agents include ethylene glycol stearates, both mono and distearate, but in one aspect, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents. Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl dimethyl amine oxides, e.g., stearyl dimethyl amine oxide. Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Personal Cleansing Compositions

The delivery particle of the current invention can be used in personal cleansing compositions to provide one or more benefits, including freshness and/or softness. The personal cleansing care compositions of the present invention can be in different forms. Non-limiting examples of said forms are: bar soap, body wash, moisturizing body wash, shower gels, skin cleansers, cleansing milks, in shower body moisturizer, shaving preparations, cleansing compositions used in conjunction with a disposable cleansing cloth, sprays, liquids, pastes, Newtonian or non-Newtonian fluids, gels, and sols.

The personal cleansing composition preferably comprises delivery particles at least comprising one benefit agent at a level where upon directed use, promotes one or more benefits. In one embodiment of the present invention, said personal cleansing composition comprises between about 0.01 wt % to about 15 wt % of at least one benefit agent encapsulated in said delivery particle. In another embodiment, said personal cleansing composition comprises between about 0.05% to about 8% of at least one benefit agent encapsulated. In another embodiment, said personal cleansing composition comprises between about 0.1% to about 5% of at least one benefit agent encapsulated.

In addition to at least one delivery particle, the personal cleansing compositions of the present invention may also include additional ingredients.

Personal cleansing compositions can be multi-phase or single phase. While the components for personal cleansing compositions will be discussed below as being multi-phase for simplicity, the components for each phase could also be used in a single phase. A personal cleansing composition can comprise a cleansing phase and a benefit phase. The cleansing phase and the benefit phase can be blended. The cleansing phase and the benefit phase can also be patterned (e.g. striped and/or marbled). In embodiments, the cleansing phase may comprise the delivery particle. In embodiments, the benefit phase may comprise the delivery particle.

Cleansing Phase

A personal cleansing composition can comprise from about 50% to about 99.5%, by weight of the composition, of a cleansing phase. A cleansing phase can include a surfactant. The personal care composition can further comprise from 2% to 20%, by weight of the rinse-off personal care composition, of a surfactant. Surfactants can comprise anionic surfactants, nonionic surfactants, amphoteric surfactants, zwitterionic surfactants, cationic surfactants, or mixtures thereof. The personal care composition can include at least one anionic surfactant. A personal care composition can also comprise, for example, an anionic surfactant, amphoteric surfactant, and a zwitterionic surfactant. Suitable amphoteric or zwitterionic surfactants, for example, can include those described in U.S. Pat. Nos. 5,104,646 and 5,106,609.

Anionic surfactants suitable for use in the cleansing phase of the present compositions include alkyl and alkyl ether sulfates. These materials have the respective formula $ROSO_3M$ and $RO(C_2H_4O)_xSO_3M$, wherein R is alkyl or alkenyl of from about 8 to about 24 carbon atoms, wherein x is about 1 to about 10, and M is a water-soluble cation such as ammonium, sodium, potassium, or triethanolamine. The alkyl ether sulfates are typically made as condensation products of ethylene oxide and monohydric alcohols having from about 8 to about 24 carbon atoms. R may have from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil may be used. Such alcohols may be reacted with about 1 or about 3 to about 10 or about 5 molar proportions of ethylene oxide. The resulting mixture of molecular species may have, for example, an average of 3 moles of ethylene oxide per mole of alcohol, is sulfated and neutralized.

Other suitable anionic surfactants include water-soluble salts of the organic, sulfuric acid reaction products of the general formula $[R^1—SO_3-M]$, wherein $R^1$ is chosen from the group consisting of a straight or branched chain, saturated aliphatic hydrocarbon radical having from about 8 to about 24, or about 10 to about 18, carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Suitable anionic surfactants for use in the cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Anionic surfactants with branched alkyl chains such as sodium trideceth sulfate, for example, may be employed. Mixtures of anionic surfactants can also be used.

Amphoteric surfactants can include those that can be broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic surfactants suitable for use as cleansing surfactant in the structured aqueous cleansing phase include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate.

Other zwitterionic surfactants suitable for use in the cleansing phase include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gammacarboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH$(CH_2)_3$ radical is attached to the nitrogen atom of the betaine are also useful in the present compositions.

Amphoacetates and diamphoacetates can also be used. Non-limiting examples of suitable amphoacetates and diamphoacetates include sodium lauroamphoacetate, sodium cocoamphoactetate, disodium lauroamphoacetate, and disodium cocodiamphoacetate.

Cationic surfactants can also be used in the cleansing phase and may represent from 2% to about 5%, by weight of the cleansing phase.

Suitable nonionic surfactants for use in structured aqueous cleansing phase include condensation products of alkylene oxide groups (hydrophilic in nature) with an organic hydrophobic compound, which may be aliphatic or alkyl aromatic in nature.

Other suitable surfactants or cosurfactants that can generally be used in a cleansing phase for a rinse-off personal care composition are described in McCutcheon's: Detergents and Emulsifiers North American Edition (Allured Publishing Corporation 1947) (1986), McCutcheon's, Functional Materials North American Edition (Allured Publishing Corporation 1973) (1992) and U.S. Pat. No. 3,929,678 (filed Aug. 1, 1974).

The cleansing phase can include a structuring surfactant. Such a structuring surfactant can be included from 2% to about 20%, by weight of the personal care composition; from about 3% to about 15%, by weight of the personal care composition; or from about 5% to about 10%, by weight of the personal care composition. Such a structuring surfactant can include sodium trideceth(n) sulfate, hereinafter STnS, wherein n defines the average moles of ethoxylation. n can range, for example, from about 0 to about 3; n can range from about 0.5 to about 2.7; from about 1.1 to about 2.5; from about 1.8 to about 2.2; or n can be about 2. When n is less than 3, STnS can provide improved stability, improved compatibility of benefit agents within the rinse-off personal care compositions, and/or increased mildness of the rinse-off personal care compositions, such described benefits of STnS are disclosed in U.S. Patent Application Pub. No. 2012/0009285.

The personal care composition can further comprise from about 2% to 20%, by weight of the personal care composition, of a cosurfactant. Cosurfactants can comprise amphoteric surfactants, zwitterionic surfactants, or mixtures thereof. Examples of these types of surfactant are discussed above.

The personal care composition can also comprise a water-soluble cationic polymer. The water-soluble cationic polymer can be present from about 0.001 to about 3 percent by weight of the personal care composition. The water-soluble cationic polymer can also be present from about 0.05 to about 2 percent by weight of the personal care composition. The water-soluble cationic polymer can also be present from about 0.1 to about 1 by weight of the personal care composition. The polymer may be in one or more phases as a deposition aid for the benefit agents described herein. Suitable cationic deposition polymers for use in the compositions of the present invention contain, for example, cationic nitrogen-containing moieties such as quaternary ammonium or cationic protonated amino moieties. The cationic protonated amines can be primary, secondary, or tertiary amines depending upon the particular species and the selected pH of the personal care composition.

Nonlimiting examples of cationic deposition polymers for use in compositions include polysaccharide polymers, such as cationic cellulose derivatives. The cationic cellulose polymers can be, for example, the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers. The water-soluble cationic polymer comprises, for example, KG-30M. Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Ashland.

The water-soluble cationic polymer can comprise, for example, a cationic guar. In one example, the cationic guar comprises guar hydroxypropyltrimonium chloride. The guar hydroxypropyltrimonium chloride can comprise, for example, N-hance™ CG-17 Cationic Guar. The cationic guar can be, for example, selected from a group consisting of N-hance™ 3196, Jaguar C-500, Jaguar C-17, and a combination thereof. Deposition polymers can have a cationic charge density from about 0.8 meq/g to about 2.0 meq/g or from about 1.0 meq/g to about 1.5 meq/g, or about 0.96 meq/g.

The water-soluble cationic polymer can also comprise synthetic polyacrylamides. Examples of suitable synthetic polyacrylamides include polyquaternium 76 and Polymethylene-bis-acrylamide methacrylamido propyltrimethyl ammonium chloride (PAMMAPTAC, AM:MAPTAC ratio 88:12. In one example, the water-soluble cationic polymer comprises PAM/MAPTAC.

A cleansing phase of a personal care composition can also include an associative polymer. Such associative polymer can be a crosslinked, alkali swellable, associative polymer comprising acidic monomers and associative monomers with hydrophobic end groups, whereby the associative polymer comprises a percentage hydrophobic modification and a hydrophobic side chain comprising alkyl functional groups. Without intending to be limited by theory, it is believed the acidic monomers can contribute to an ability of the associative polymer to swell in water upon neutralization of acidic groups; and associative monomers anchor the associative polymer into structured surfactant hydrophobic domains, e.g., lamellae, to confer structure to the surfactant phase and keep the associative polymer from collapsing and losing effectiveness in a presence of an electrolyte.

The crosslinked, associative polymer can comprise a percentage hydrophobic modification, which is a mole percentage of monomers expressed as a percentage of a total number of all monomers in a polymer backbone, including both acidic and other non-acidic monomers. Percentage hydrophobic modification of the associative polymer, hereafter % HM, can be determined by the ratio of monomers added during synthesis, or by analytical techniques such as proton nuclear magnetic resonance (NMR). Associative alkyl side chains can comprise, for example, butyl, propyl, stearyl, steareth, cetyl, lauryl, laureth, octyl, behenyl, beheneth, steareth, or other linear, branched, saturated, or unsaturated alkyl or alketh hydrocarbon side chains. The acidic monomer can comprise any acid functional group, for example sulfate, sulfonate, carboxylate, phosphonate, or phosphate or mixtures of acid groups. The acidic monomer can comprise, for example, a carboxylate, alternatively the acidic monomer is an acrylate, including acrylic acid and/or methacrylic acid. The acidic monomer comprises a polymerizable structure, e.g., vinyl functionality. Mixtures of acidic monomers, for example acrylic acid and methacrylic acid monomer mixtures, are useful.

The associative monomer can comprise a hydrophobic end group and a polymerizable component, e.g., vinyl, which can be attached. The hydrophobic end group can be attached to the polymerizable component, hence to the polymer chain, by different means but can be attached by an ether or ester or amide functionality, such as an alkyl acrylate or a vinyl alkanoate monomer. The hydrophobic end group can also be separated from the chain, for example, by an alkoxy ligand such as an alkyl ether. The associative monomer can be, for example, an alkyl ester, an alkyl (meth)acrylate, where (meth)acrylate is understood to mean either methyl acrylate or acrylate, or mixtures of the two.

The hydrophobic end group of the associative polymer can be incompatible with the aqueous phase of the composition and can associate with lathering surfactant hydrophobe components. Without intending to be limited by theory, it is believed that longer alkyl chains of structuring polymer hydrophobe end groups can increase incompatibility with the aqueous phase to enhance structure, whereas somewhat shorter alkyl chains having carbon numbers closely resembling lathering surfactant hydrophobes (e.g., 12 to 14 carbons) or multiples thereof (for bilayers, e.g.) can also be effective. An ideal range of hydrophobic end group carbon numbers combined with an optimal percentage of hydrophobic monomers expressed as a percentage of the polymer backbone can provide increased structure to the lathering, structured surfactant composition at low levels of polymer structurant.

Other optional additives can be included in the cleansing phase, including for example an emulsifier (e.g., non-ionic emulsifier) and electrolytes. Suitable emulsifiers and electrolytes are described in U.S. patent application Ser. No. 13/157,665.

Personal Care Composition Benefit Phase

As noted herein, personal care compositions can include a benefit phase. The composition may comprise from about 0.1% to about 50%, by weight of the composition, of a benefit phase. The benefit phase can be hydrophobic and/or anhydrous. The benefit phase can also be substantially free of or free of surfactant. In particular, the benefit phase can comprise from about 0.1% to about 50%, by weight of the rinse-off personal care composition, of a benefit agent. The benefit phase can include, for example, from about 0.5% to about 20%, by weight of the rinse-off personal care composition, of a benefit agent.

A benefit phase can have a particle size of about 4 to about 500 μm, from about 5 to about 300 μm, from about 6 to about 100 μm, or from about 10 to about 50 μm. The particle size is measured in neat product under a differential interference contrast optical microscope with a 10× objective lens. The particle size distribution is counted manually. All benefit phase particles are assumed as uniform spheres in this application. For irregular shaped benefit phase particles, the longest axis is used as the diameter for the particle size distribution counting. The number weighted average of all lipid particles is defined as the average lipid particle size. This measurement can also be accomplished with a computer algorithm.

A benefit phase can have a viscosity as measured by a standard rheometer, such as a Brookfield R/S plus. A sample of 2.5 mL is measured with a spindle C75-1 at a shear rate of $2\ s^{-1}$ at 25° C. A benefit phase can generally have a viscosity of about 200 cP to about 15,000 cP.

A benefit agent can include a liquid benefit agent. A liquid benefit agent is considered liquid if that is its natural state at room temperature (i.e. 23° C.). A liquid benefit agent can have a viscosity of less than about 1000 cP, less than about 800 cP, or less than about 600 cP, and can be measured with a standard rheometer.

The benefit agent may also be non-liquid. Some examples of non-liquid benefit agents include hydrocarbons. Non-limiting examples of hydrocarbons suitable for use as non-liquid benefit agents herein can include petrolatum, microcrystalline wax, polyalkanes, polyolefins, and combinations thereof.

Other suitable benefit agents are described in U.S. Patent Application Publication No. 2012/0009285.

The benefit phase may also comprise a crystalline hydrophobic ethylene copolymer. The ethylene copolymers are random copolymers and may be present from about 0.01% to about 5% by weight of the personal care composition. The crystalline hydrophobic ethylene copolymer may be present from about 0.05% to about 2% by weight of the personal care composition. As another example, the crystalline hydrophobic ethylene copolymer may be present from about 0.1% to about 1.5% by weight of the personal care composition.

Additional Ingredients

Additional ingredients can also be added to the personal care composition for treatment of the skin and/or hair, or to modify the aesthetics of the personal care composition as is the case with perfumes, colorants, dyes or the like. Materials useful in products herein can be categorized or described by their cosmetic and/or therapeutic benefit or their postulated mode of action or function. However, it can be understood that actives and other materials useful herein can, in some instances, provide more than one cosmetic and/or therapeutic benefit or function or operate via more than one mode of action. Therefore, classifications herein can be made for convenience and cannot be intended to limit an ingredient to particularly stated application or applications listed. A precise nature of these additional materials, and levels of incorporation thereof, will depend on the physical form of the composition and the nature of the cleansing operation for which it is to be used. The additional materials can usually be formulated at about 6% or less, about 5% or less, about 4% or less, about 3% or less, about 2% or less, about 1% or less, about 0.5% or less, about 0.25% or less, about 0.1% or less, about 0.01% or less, or about 0.005% or less of the rinse-off personal care composition.

To further improve stability under stressful conditions such as high temperature and vibration, densities of separate phases can be adjusted such that they can be substantially equal. To achieve this, low density microspheres can be added to one or more phases of the rinse-off personal care composition. Examples of rinse-off personal care compositions that comprise low density microspheres are described in a patent application published on May 13, 2004 under U.S. Patent Publication No. 2004/0092415A1 entitled "Striped Liquid Personal Cleansing Compositions Containing A Cleansing Phase and A Separate Phase with Improved Stability," filed on Oct. 31, 2003 by Focht, et al.

Other non-limiting ingredients that can be used in the personal care composition of the present invention can comprise an optional benefit component that can be selected from the group consisting of thickening agents; preservatives; antimicrobials; fragrances; chelators (e.g. such as those described in U.S. Pat. No. 5,487,884 issued to Bisset, et al.); sequestrants; vitamins (e.g. Retinol); vitamin derivatives (e.g. tocophenyl actetate, niacinamide, panthenol); sunscreens; desquamation actives (e.g. such as those described in U.S. Pat. Nos. 5,681,852 and 5,652,228 issued to Bisset); anti-wrinkle/anti-atrophy actives (e.g. N-acetyl derivatives, thiols, hydroxyl acids, phenol); anti-oxidants (e.g. ascorbic acid derivatives, tocophenol) skin soothing agents/skin healing agents (e.g. panthenoic acid derivatives, aloe vera, allantoin); skin lightening agents (e.g. kojic acid, arbutin, ascorbic acid derivatives) skin tanning agents (e.g. dihydroxyacteone); anti-acne medicaments; essential oils; sensates; pigments; colorants; pearlescent agents; interference pigments (e.g such as those disclosed in U.S. Pat. No. 6,395,691 issued to Liang Sheng Tsaur, U.S. Pat. No. 6,645,511 issued to Aronson, et al., U.S. Pat. No. 6,759,376 issued to Zhang, et al, U.S. Pat. No. 6,780,826 issued to Zhang, et al.) particles (e.g. talc, kolin, mica, smectite clay, cellulose powder, polysiloxane, silicas, carbonates, titanium dioxide, polyethylene beads) hydrophobically modified non-platelet particles (e.g. hydrophobically modified titanium dioxide and other materials described in a commonly owned, patent application published on Aug. 17, 2006 under Publication No. 2006/0182699A, entitled "Personal Care Compositions Containing Hydrophobically Modified Non-platelet particle filed on Feb. 15, 2005 by Taylor, et al.) and mixtures thereof. The multiphase personal care composition can comprise from about 0.1% to about 4%, by weight of the rinse-off personal care composition, of hydrophobically modified titanium dioxide. Other such suitable examples of such skin actives are described in U.S. patent application Ser. No. 13/157,665.

Shave Preparations

The delivery particle of the current invention can be used in shave preparations to provide one or more benefits, including freshness and/or cooling. The shave preparations of the present invention can be in different forms. Non-limiting examples of said forms are: shaving creams, shaving gels, aerosol shaving gels, shaving soaps, aerosol shaving foams, liquids, pastes, Newtonian or non-Newtonian fluids, gels, and sols.

The shave preparation preferably comprises at least one benefit agent encapsulated in said delivery particle at a level where upon directed use, promotes one or more benefits. In one embodiment of the present invention, said shave preparation comprises between about 0.01% to about 15% of at least one benefit agent encapsulated in said delivery particle. In another embodiment, said shave preparation comprises between about 0.05% to about 8% of at least one benefit agent encapsulated. In another embodiment, said shave preparation comprises between about 0.1% to about 5% of at least one benefit agent encapsulated.

In addition to at least one delivery particle, the shave preparations of the present invention may also include lathering surfactants, carriers, adjunct ingredients, and other additional ingredients.

Lathering Surfactants

The shave preparations can comprise one or more lathering surfactants and a carrier such as water, at a total level of from about 60% to about 99.99%. A lathering surfactant defined herein as surfactant, which when combined with water and mechanically agitated generates a foam or lather. Preferably, these surfactants or combinations of surfactants should be mild, which means that these surfactants provide sufficient cleansing or detersive benefits but do not overly dry the skin or hair while still being able to produce a lather.

A wide variety of lathering surfactants are useful herein and include those selected from the group consisting of anionic lathering surfactants, nonionic lather surfactants, amphoteric lathering surfactants, and mixtures thereof. Generally, the lathering surfactants are fairly water-soluble. When used in the composition, at least about 4% of the lathering surfactants have a HLB value greater than about ten. Examples of such surfactants are found in and U.S. Pat. No. 5,624,666. Cationic surfactants can also be used as optional components, provided they do not negatively impact the overall lathering characteristics of the required lathering surfactants.

Concentrations of these surfactant are from about 10% to about 20%, alternatively from about 5% to about 25%, and alternatively from 2% to about 60% by weight of the composition.

Anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678. A wide variety of anionic lathering surfactants are useful herein. Non-limiting examples of anionic lathering surfactants include those selected from the group consisting of sarcosinates, sulfates, sulfonates, isethionates, taurates, phosphates, lactylates, glutamates, and mixtures thereof.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms, mono-alkyl, dialkyl, and trialkylphosphate salts, alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine). Also useful are taurates which are based on taurine, which is also known as 2-aminoethanesulfonic acid, and glutamates, especially those having carbon chains between $C_8$ and $C_{16}$.

Suitable amphoteric or zwitterionic detersive surfactants for use in the compositions herein include those which are known for use in hair care or other personal care cleansing. Concentration of such amphoteric detersive surfactants is from about 1% to about 10%, alternatively from about 0.5% to about 20% by weight of the composition. Non-limiting examples of suitable zwitterionic or amphoteric surfactants are described in U.S. Pat. Nos. 5,104,646 and 5,106,609.

Nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety. Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, sodium myristoyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

One suitable lathering surfactant is a polyglyceryl fatty ester. In one embodiment the polyglyceryl fatty ester surfactant has the formula:

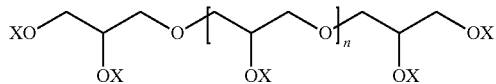

wherein n is an integer from 1 to 10, and X is a hydrogen atom or a long chain acyl group derived from a $C_{12-22}$ fatty acid or an N-fatty acyl-neutral amino acid, provided that at least one X is a long chain acyl group and no more than three X's are long chain acyl groups. In one embodiment, the polyglyceryl fatty ester surfactant is selected from the group consisting of: polyglyceryl-10 oleate, polyglyceryl-6 stearate, polyglyceryl-10 stearate, polyglyceryl-8 dipalmitate, polyglyceryl-10 dipalmitate, polyglyceryl-10 behenate, and polyglyceryl-12 trilaurate.

Carriers

The shave preparation of the present invention can also comprise a carrier. In one embodiment the carrier comprises water. The carrier is preferably dermatologically acceptable, meaning that the carrier is suitable for topical application to the keratinous tissue, has good aesthetic properties, is compatible with the actives of the present invention and any other components, and will not cause any safety or toxicity concerns. In one embodiment, the shave preparation comprises from 50% to about 99.99%, preferably from about 60% to about 99.9%, more preferably from about 70% to about 98%, and even more preferably from about 80% to about 95% of the carrier by weight of the composition.

Adjunct Ingredients

Lubricants

In one embodiment, said shave preparation comprises at least one lubricant selected from: a lubricious water-soluble polymer, a water insoluble particle, a hydrogel forming polymer, and a mixture thereof.

The lubricious water-soluble polymer will generally have a molecular weight greater between about 300,000 and 15,000,000 daltons, preferably more than about one million daltons, and will include a sufficient number of hydrophilic moieties or substituents on the polymer chain to render the polymer water-soluble. The polymer may be a homopolymer, copolymer or terpolymer. Examples of suitable lubricious water-soluble polymers include polyethylene oxide, polyvinylpyrrolidone, and polyacrylamide. A preferred lubricious water-soluble polymer comprises polyethylene oxide, and more particularly a polyethylene oxide with a molecular weight of about 0.5 to about 5 million daltons. Examples of suitable polyethylene oxides PEG-23M, PEG-45M, and PEG-90M. The lubricious water-soluble polymer can be at a level of about 0.005% to about 3%, preferably about 0.01% to about 1%, by weight.

The water insoluble particles may include inorganic particles or organic polymer particles. Examples of inorganic particles include titanium dioxide, silicas, silicates and glass beads, with glass beads being preferred. Examples of organic polymer particles include polytetrafluoroethylene particles, polyethylene particles, polypropylene particles, polyurethane particles, polyamide particles, or mixtures of two or more of such particles.

The hydrogel-forming polymer is a highly hydrophilic polymer that, in water, forms organized three-dimensional domains of approximately nanometer scale. The hydrogel-forming polymer generally has a molecular weight greater than about one million daltons (although lower molecular weights are possible) and typically is at least partially or lightly crosslinked and may be at least partially water insoluble, but it also includes a sufficient number of hydrophilic moieties so as to enable the polymer to trap or bind a substantial amount of water within the polymer matrix and thereby form three-dimensional domains. Generally, the hydrogel-forming polymer will be included in the shaving composition in an amount of about 0.0005% to about 3%, or about 0.001% to about 0.5%, or about 0.002% to about 0.1%, by weight.

The term "water dispersible", as used herein, means that a substance is either substantially dispersible or soluble in water. The water dispersible surface active agent is preferably one that is capable of forming a lather, such as one or more of the optional lathering surfactants described in section 5 below (including but not limited to a soap, an interrupted soap, a detergent, an anionic surfactant, a nonionic surfactant or a mixture of one or more of these.)

Polar Solvents

In one embodiment, the carrier comprises a polar solvent. The level of polar solvent can be from about 1% to about 20%, or from about 5% to about 10%. Polar solvents useful herein include polyhydric alcohols such as 1,3-butylene glycol, propane diol, ethylene glycol, diethylene glycol, sorbitol, and other sugars which are in liquid form at ambient temperature glycerin, sorbitol, propylene glycol, butylene glycol, pentylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Polyols such as those containing from 2 to about 6 carbon atoms and from 2 to about 6 hydroxy groups are preferred (e.g., 1,3-propanediol, ethylene glycol, glycerin, and 1,2-propanediol) can also be used. The most preferred are Butylene, Pentylene or Hexylene Glycol and mixtures thereof.

Salicylic Acid

The shave preparation of the present invention may comprise a salicylic acid compound, its esters, its salts, or combinations thereof. In the compositions of the present invention, the salicylic acid compound preferably comprises from about 0.1% to about 5%, preferably from about 0.2% to about 2%, and more preferably from about 0.5% to about 2%, by weight of the composition, of salicylic acid.

Other Adjunct Ingredients

The compositions of the present invention may contain a variety of other ingredients that are conventionally used in given product types provided that they do not unacceptably alter the benefits of the invention. These ingredients should be included in a safe and effective amount for a shave preparation for application to skin.

Conditioning Agents

The compositions of the present invention may comprise a conditioning agent selected from the group consisting of humectants, moisturizers, or skin conditioners, each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g., ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, sucrose, etc.); hyaluronic acid; lactamide monoethanolamine; acetamide monoethanolamine; sucrose polyester, petrolatum; and mixtures thereof.

Suitable moisturizers, also referred to in the present invention as humectants, include urea, guanidine, glycolic acid and glycolate salts (e.g. ammonium and quaternary alkyl ammonium), lactic acid and lactate salts (e.g. ammonium and quaternary alkyl ammonium), aloe vera in any of its variety of forms (e.g. aloe vera gel), polyhydroxy alcohols (such as sorbitol, glycerol, hexanetriol, propylene glycol, hexylene glycol and the like), polyethylene glycol, sugars and starches, sugar and starch derivatives (e.g. alkoxylated glucose), hyaluronic acid, lactamide monoethanolamine, acetamide monoethanolamine, and mixtures thereof.

Thickening Agents (Including Thickeners and Gelling Agents)

The compositions of the present invention can comprise one or more thickening agents, preferably from about 0.05% to about 10%, more preferably from about 0.1% to about 5%, and even more preferably from about 0.25% to about 4%, by weight of the composition. Nonlimiting classes of thickening agents include those selected from the group consisting of: Carboxylic Acid Polymers (crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol); crosslinked polyacrylate polymers (including both cationic and nonionic polymers, such as described in U.S. Pat. Nos. 5,100,660; 4,849,484; 4,835,206; 4,628,078; 4,599,379, and EP 228,868); polymeric sulfonic acid (such as copolymers of acryloyldimethyltaurate and vinylpyrrolidone) and hydrophobically modified polymeric sulfonic acid (such as crosspolymers of acryloyldimethyltaurate and beheneth-25 methacrylate); polyacrylamide polymers (such as nonionic polyacrylamide polymers including substituted branched or unbranched polymers such as polyacrylamide and isoparaffin and laureth-7 and multi-block copolymers of acrylamides and substituted acrylamides with acrylic acids and substituted acrylic acids); polysaccharides (nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof); gums (i.e. gum agents such as acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof); and crystalline, hydroxyl-containing fatty acids, fatty esters or fatty waxes (such as microfibrous bacterial cellulose structurants as disclosed in U.S. Pat. No. 6,967,027 to Heux et al.; U.S. Pat. No. 5,207,826 to Westland et al.; U.S. Pat. No. 4,487,634 to Turbak et al.; U.S. Pat. No. 4,373,702 to Turbak et al. and 4,863,565 to Johnson et al., U.S. Patent Publ. No. 2007/0027108 to Yang et al.)

Compositional pH

The shave preparation of the present invention preferably has a pH of less than about 9, more preferably less than about 7. In one embodiment the composition has a pH of less than about 5, or less than about 4. In one preferred embodiment the composition has a pH range of from about 2.5 to about 4.5. Suitable lathering surfactants for use at pH levels below about 4 can be selected from the group consisting of alkyl sulfonates, pareth sulfonates, sulfobetaines, alkylhydroxysultaines, alkylglucosides and mixtures thereof.

Fabric Care Compositions

Fabric care compositions of the present invention may include additional adjunct ingredients that include: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments. Other variants of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers, malodor reduction materials and/or pigments. The precise nature of these additional components, and levels of incorporation thereof, will depend on the physical form of the composition and the nature of the operation for which it is to be used. However, when one or more adjuncts are present, such one or more adjuncts may be present as detailed below. The following is a non-limiting list of suitable additional adjuncts.

Deposition Aid

The fabric care composition may comprise from about 0.01% to about 10%, from about 0.05 to about 5%, or from about 0.15 to about 3% of a deposition aid. The deposition aid may be a cationic or amphoteric polymer. The deposition aid may be a cationic polymer. Cationic polymers in general and their method of manufacture are known in the literature. The cationic polymer may have a cationic charge density of from about 0.005 to about 23 meq/g, from about 0.01 to about 12 meq/g, or from about 0.1 to about 7 meq/g, at the pH of the composition. For amine-containing polymers, wherein the charge density depends on the pH of the composition, charge density is measured at the intended use pH of the product. Such pH will generally range from about 2 to about 11, more generally from about 2.5 to about 9.5. Charge density is calculated by dividing the number of net charges per repeating unit by the molecular weight of the repeating unit. The positive charges may be located on the backbone of the polymers and/or the side chains of polymers.

The weight-average molecular weight of the polymer may be from about 500 Daltons to about 5,000,000 Daltons, or from about 1,000 Daltons to about 2,000,000 Daltons, or from about 2,500 Daltons to about 1,500,000 Daltons, as determined by size exclusion chromatography relative to polyethylene oxide standards with RI detection. The weight-average molecular weight of the cationic polymer may be from about 500 Daltons to about 37,500 Daltons.

Surfactants: Surfactants utilized can be of the anionic, nonionic, zwitterionic, ampholytic or cationic type or can comprise compatible mixtures of these types, as described above in relation to HAIR CARE, PERSONAL CARE, and SHAVE CARE Compositions. Anionic and nonionic surfactants are typically employed if the fabric care product is a laundry detergent. On the other hand, cationic surfactants are typically employed if the fabric care product is a fabric softener. In addition to the anionic surfactant, the fabric care compositions of the present invention may further contain a nonionic surfactant. The compositions of the present invention can contain up to about 30%, alternatively from about 0.01% to about 20%, more alternatively from about 0.1% to about 10%, by weight of the composition, of a nonionic surfactant. The nonionic surfactant may comprise an ethoxylated nonionic surfactant. Suitable for use herein are the ethoxylated alcohols and ethoxylated alkyl phenols of the formula $R(OC_2H_4)n$ OH, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

The fabric care compositions of the present invention may contain up to about 30%, alternatively from about 0.01% to about 20%, more alternatively from about 0.1% to about 20%, by weight of the composition, of a cationic surfactant. For the purposes of the present invention, cationic surfactants include those which can deliver fabric care benefits. Non-limiting examples of useful cationic surfactants include: fatty amines; quaternary ammonium surfactants; and imidazoline quat materials.

Non-limiting examples of fabric softening actives are N,N-bis(stearoyl-oxy-ethyl) N,N-dimethylammonium chloride; N,N-bis(tallowoyl-oxy-ethyl) N,N-dimethylammonium chloride, N,N-bis(stearoyl-oxy-ethyl)N-(2 hydroxyethyl)N-methyl ammonium methyl sulfate; 1, 2 di (stearoyl-oxy) 3 trimethyl ammoniumpropane chloride; dialkylenedimethylammonium salts such as dicanoladimethylammonium chloride, di(hard)tallowdimethylammonium chloride dicanoladimethylammonium methyl sulfate; 1-methyl-1-stearoylamidoethyl-2-stearoylimidazolinium methyl sulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

It will be understood that combinations of softener actives disclosed above are suitable for use herein.

Builders

The compositions may also contain from about 0.1% to 80% by weight of a builder. Compositions in liquid form generally contain from about 1% to 10% by weight of the builder component.

Compositions in granular form generally contain from about 1% to 50% by weight of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions comprising a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from about 0.5 to about 4.0, or from about 1.0 to about 2.4. Also useful are aluminosilicates including zeolites.

Dispersants

The compositions may contain from about 0.1%, to about 10%, by weight of dispersants. Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes

The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5%. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents

The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant

The compositions may contain less than about 5%, or from about 0.01% to about 3% of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Bleach System

Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-sulphonate, benzoylvalerolactam, dodecanoyloxybenzenesulphonate. Other bleaching agents include metal complexes of transitional metals with ligands of defined stability constants.

Stabilizer

The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Silicones

Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. The organosilicones may comprise a viscosity of from about 10 to about 2,000,000 centistokes at 25° C. Suitable organosilicones may have a viscosity of from about 10 to about 800,000 centistokes at 25° C.

Test Methods

It is understood the test methods disclosed in the TEST METHODS Section should be used to determine the respective values of the parameters described and claimed in the present application.

1. Method for Treating Fabrics with Fabric Softener/Liquid Laundry Detergent Composition Prior to Head Space Concentration Determination The method to treat fabrics with fabric softener composition comprises a fabric pretreatment phase followed by a fabric treatment phase.

Fabric Pretreatment Phase:

2.9±0.1 kg of ballast fabrics containing cotton, polyester, polycotton, 3 white knitted cotton fabric tracers (from Warwick Equest) and 3 white polyester tracers are washed 4 times with 50 g Non-perfumed Ariel Sensitive (Nordics) at 60° C. with 2 grains per gallon (gpg) water, 1 h 26 min cycle, 1600 rpm, in a front loader washing machine such as Miele (Novotronic W986/Softronic W467/W526/W527/W1614/W1714/W2261) or equivalent and then washed once with no detergent at 60° C. with 2 gpg water. After the last wash, fabrics are dried in a 5 kg drum tumble drier with hot air outlet such as Miele Novotronic (T490/T220/T454/T430/T410/T7634) or equivalent and then they are ready to be used for testing.

Fabric Treatment Phase:

2.9±0.1 kg of ballast fabrics containing cotton, polyester, polycotton, 3 white knitted cotton fabric tracers (from Warwick Equest) and 3 white polyester tracers are washed in 15 gpg water under different conditions depending on the product to be tested:

1. at 40° C., 1 h 24 minutes cycle, 1200 rpm without laundry detergent to avoid interference in the fabric softener evaluation. Liquid fabric softener composition is pre-diluted in 2 L of 15° C. water with a hardness of 15 gpg 5 min before the starting of the last rinse and added to the last rinse while the washing machine is taking the water. This is a requirement to ensure homogeneous dispensability over the load and minimize the variability of the test results. All fabrics are line dried in a control temperature (25° C.) and humidity (60%) room for 24 hours prior to head space concentration determination; or 2. at 30° C., 1 h 15 minutes cycle, 1000 rpm using the laundry detergent to be evaluated without fabric softener. The laundry detergent is dosed in a dosing ball and introduced in the tumble together with the fabrics.

2. Method for Determining Head Space Concentration

Three white knitted cotton fabric tracers and/or 3 white polyester fabric tracers treated with fabric softener compositions (see Method for treating fabrics with fabric softener composition prior to head space concentration determination) are used for the analysis. A piece of 5×5 cm is gently cut from the center of each fabric tracer and analyzed by fast head space gas chromatography/mass spectroscopy ("GC/MS") using an Agilent DB-5UI 30 m×0.25×0.25 column (part #122-5532UI) in splitless mode. Each fabric tracer cut is transferred into 25 mL glass headspace vials. The fabric samples are allowed to equilibrate for 10 minutes at 65° C. before the headspace above the fabrics is sampled using a 23 gauge 50/30UM DVB/CAR/PDMS SPME fiber (Sigma-Aldrich part #57298-U) for 5 minutes. The SPME fiber is subsequently on-line thermally desorbed into the GC using a ramp from 40° C. (0.5 min) to 270° C. (0.25 min) at 17° C./min. The perfume raw materials with a molecular weight between 35 and 300 m/z are analyzed by fast GC/MS in full scan mode. The amount of perfume in the headspace is expressed as nmol/L.

3. Sample Preparation for Biodegradability Measurements

The water-soluble or water dispersible material is purified via crystallization till a purity of above 95% is achieved and dried before biodegradability measurement.

The oily medium comprising the benefit agent needs to be extracted from the delivery particle slurry in order to only analyse the polymer wall. Therefore, the delivery particle slurry is washed between 3 and 10 times with water to remove all soluble polymers that are not reacted in the polymer wall, such as colloids and depositions aids. Then, it is further washed with organic solvents to extract the oily medium comprising the benefit agent till weight percentage of oily medium is below 5% based on total delivery particle polymer wall. Finally, the polymer wall is dried and analysed.

Weight ratio of delivery particle:solvent is 1:3. Residual oily medium is determined by thermogravimetric analysis (60 minutes isotherm at 100° C. and another 60 min isotherm at 250° C.). The weight loss determined needs to be below 5%.

4. OECD 301 B—Biodegradability Method

Accumulative $CO_2$ release is measured over 60 days following the guidelines of the Organisation for Economic Cooperation and Development (OECD)—OECD (1992), Test No. 301: Ready Biodegradability, OECD Guidelines for the Testing of Chemicals, Section 3, OECD Publishing, Paris, https://doi.org/10.1787/9789264070349-en.

5. Leakage

The amount of benefit agent leakage from the benefit agent containing delivery particles is determined according to the following method:
a) Obtain two 1 g samples of the raw material slurry of benefit agent containing delivery particles.
b) Add 1 g of the raw material slurry of benefit agent containing delivery particles to 99 g of the consumer product matrix in which the particles will be employed and label the mixture as Sample 1. Immediately use the second 1 g sample of raw material particle slurry in Step d below, in its neat form without contacting consumer product matrix, and label it as Sample 2.
c) Age the delivery particle-containing product matrix (Sample 1) for 1 week at 35° C. in a sealed glass jar.
d) Using filtration, recover the particles from both samples. The particles in Sample 1 (in consumer product matrix) are recovered after the aging step. The particles in Sample 2(neat raw material slurry) are recovered at the same time that the aging step began for sample 1.
e) Treat the recovered particles with a solvent to extract the benefit agent materials from the particles.
f) Analyse the solvent containing the extracted benefit agent from each sample, via chromatography.
g) Integrate the resultant benefit agent peak areas under the curve and sum these areas to determine the total quantity of benefit agent extracted from each sample.
h) Determine the percentage of benefit agent leakage by calculating the difference in the values obtained for the total quantity of benefit agent extracted from Sample 2 (S2) minus Sample 1 (S1), expressed as a percentage of the total quantity of benefit agent extracted from Sample 2 (s2), as represented in the equation below:

$$\% \text{ Leakage} = \left(\frac{S2 - S1}{S2}\right) \times 100$$

6. Volume Weighted Median Particle Size

Particle size is measured using static light scattering devices, such as an Accusizer 780A, made by Particle Sizing Systems, Santa Barbara Calif. The instrument is calibrated from 0 to 300 μ using Duke particle size standards. Samples for particle size evaluation are prepared by diluting about 1 g emulsion, if the volume weighted median particle size of the emulsion is to be determined, or 1 g of benefit agent containing delivery particles slurry, if the finished particles volume weighted median particle size is to be determined, in about 5 g of de-ionized water and further diluting about 1 g of this solution in about 25 g of water.

About 1 g of the most dilute sample is added to the Accusizer and the testing initiated, using the autodilution feature. The Accusizer should be reading in excess of 9200 counts/second. If the counts are less than 9200 additional sample should be added. The accusizer will dilute the test sample until 9200 counts/second and initiate the evaluation. After 2 minutes of testing the Accusizer will display the results, including volume-weighted median size.

The broadness index can be calculated by determining the particle size at which 95% of the cumulative particle volume is exceeded (95% size), the particle size at which 5% of the cumulative particle volume is exceeded (5% size), and the median volume-weighted particle size (50% size–50% of the particle volume both above and below this size). Broadness Index=((95% size)–(5% size)/50% size).

7. Gel Permeation Chromatography with Multi-Angle Light Scattering and Refractive Index Detection (GPC-MALS/RI) for Polymer Molecular Weight Distribution Measurement Gel Permeation Chromatography (GPC) with Multi-Angle Light Scattering (MALS) and Refractive Index (RI) Detection (GPC-MALS/RI) permits the measurement of absolute molecular weight of a polymer without the need for column calibration methods or standards. The GPC system allows molecules to be separated as a function of their molecular size. MALS and RI allow information to be obtained on the number average (Mn) and weight average (Mw) molecular weight. The Mw distribution of water-soluble polymers like polyvinylalcohol, polysaccharides, polyacrylates materials is typically measured by using a Liquid Chromatography system (e.g., Agilent 1260 Infinity pump system with OpenLab Chemstation software, Agilent Technology, Santa Clara, CA, USA) and a column set (e.g., Waters ultrahydrogel guard column, 6 mm ID×40 mm length, two ultrahydrogel linear columns, 7.8 mm ID×300 mm length, Waters Corporation of Milford, Mass., USA) which is operated at 40° C. The mobile phase is 0.1M sodium nitrate in water containing 0.02% sodium azide and is pumped at a flow rate of 1 mL/min, isocratically. A multiangle light scattering (MALS) detector DAWN® and a differential refractive index (RI) detector (Wyatt Technology of Santa Barbara, Calif., USA) controlled by Wyatt Astra® software are used. A sample is typically prepared by dissolving polymer materials in the mobile phase at ~1 mg per ml and by mixing the solution for overnight hydration at room temperature. The sample is filtered through a 0.8 μm Versapor membrane filter (PALL, Life Sciences, NY, USA) into the LC autosampler vial using a 3-ml syringe before the GPC analysis. A dn/dc (differential change of refractive index with concentration) value is measured on the polymer materials of interest and used for the number average and weight average molecular weights determination by the Astra detector software.

EXAMPLES

Example 1: Fragrance Oil Delivery Particles Comprising Chitosan and Poly(Vinyl Alcohol) Covalently Bounded to the Polyacrylic Wall Material Samples 1-8:

A first composition was prepared in a 300 mL beaker by mixing 156.59 g of Fragrance Oil, 0.21 g of 2-carboxyethyl acrylate (Merck), 4.50 g CN975—hexafunctional aromatic urethane acrylate oligomer—(Sartomer), 0.40 g 2,2-azobis(2,4-dimethylvaleronitrile) (Chemours) and 0.09 g 2,2-azobis(2-methylbutyronitrile) (Chemours) at 25° C. via magnetic stirring. Then, 78.21 g of isopropyl myristate (BASF) was added to the solution at 25° C. and mixed for 15 minutes with a magnetic stirrer till a homogeneous composition was obtained.

A second composition was prepared comprising 355.28 g of a 2 wt % Selvol 540 poly(vinyl alcohol) (Sekisui) aqueous solution (348.17 g distilled water and 7.11 g Selvol540), 1.79 g acetic acid (0.5 wt %) and Chitoclear (Primex) at 25° C. via magnetic stirring. Once Chitoclear was fully dissolved the persulfate initiator was added and dissolved by mixing for 1 hour with magnetic stirrer at 25° C., as shown in Samples 1-8 in TABLE 1 below.

The first composition was added to the second composition and emulsified using an overhead mixer (such as IKA overhead mixer) at 1200 rpm for 30 minutes with a 90 degrees 4 blades stirrer. Then the emulsion was transferred to a 1 L coated reactor equipped with reflux condenser and overhead stirrer with anchor type impeller. Mixing was kept at 180 rpm for 14 h with following temperature ramp: i) temperature was first increased to 60° C. in 15 minutes and held at 60° C. for 45 minutes; ii) temperature was increased to 75° C. in 30 minutes, 1.33 g of 4,4-azobis(4-cyanovaleric acid) (Chemours) was added and the mixture held at 75° C. for 4 hours; iii) temperature was increased to 90° C. in 30 minutes and held at 90° C. for 8 hours. The batch was then cooled to 20° C. and used without further treatment.

TABLE 1

| Sample | Radical initiator | % radical initiator | % chitosan in the water solution |
|---|---|---|---|
| 1 | Potassium persulfate | 0.70 | 0.50 |
| 2 | Ammonium persulfate | 0.70 | 0.50 |
| 3 | Sodium persulfate | 0.70 | 0.50 |
| 4 | Potassium persulfate | 0.70 | 1.00 |
| 5 | Potassium persulfate | 0.35 | 1.00 |
| 6 | Ammonium persulfate | 0.35 | 1.00 |
| 7 | Sodium persulfate | 0.35 | 1.00 |
| 8 | Potassium persulfate | 0.35 | 0.50 |

Sample 8, has a biodegradability of 58% $CO_2$ (Method 4)

Sample 9:

A water phase was prepared by mixing 272 g demineralized water, 184 g of a 5 wt % aqueous solution of Selvol 540, and 2.30 g acetic acid at room temperature. To the above water phase solution, 2.30 g Chitoclear chitosan was added and mixed until it is dissolved. 1.61 g potassium persulfate was then added to the above solution and mixed until it is dissolved.

A first oil phase was prepared by mixing 22.41 g perfume oil, 3.26 g CN975, 0.039 g TBAEMA and 0.039 g CD9055 until a homogenous mixture was obtained.

A second oil phase was prepared by mixing 100.89 g of the perfume oil, 100.89 g isopropyl myristate, and 0.18 g 2,2'-azobis(2-methylbutyronitrile) in a jacketed stainless-steel reactor. The reactor was held at 35° C. and the oil solution mixed. A nitrogen blanket was applied to the reactor at a rate of 100 cc/min. The second oil composition was heated to 70° C. in 45 minutes, held at 70° C. for 45 minutes, then cooled to 50° C. in 45 minutes. Once cooled to 50° C. the first oil phase was added, and the combined oils mixed for another 10 minutes at 50° C.

The water phase was then added to the combined oil phase. High shear agitation was then applied to produce an emulsion with volume weighted median size of 27.95 μm, determined via Method 9. The reactor was then mixed with a 3" diameter marine propeller blade, 0.21 g 4,4'-azobis[4-cyanovaleric acid] and 100 g demineralized water added, covered, and the temperature increased to 75° C. in 60 minutes, held at 75° C. for 4 hours, increased to 95° C. in 60 minutes, and held at 95° C. for 6 hours. The batch was cooled to 25° C. in 90 minutes. The percentage of solids was measured at 34.81 wt %.

Sample 10:

A water phase was prepared by mixing 344.67 g demineralized water, 110.93 g of a 5 wt % aqueous solution of Selvol 540, and 2.30 g acetic acid at room temperature. To the above water phase solution, 2.30 g Chitoclear chitosan was added and mixed until it is dissolved. 1.61 g potassium persulfate was then added to the above solution and mixed until it is dissolved.

A first oil phase was prepared by mixing 22.41 g perfume oil, 4.00 g CN975, 0.048 g TBAEMA and 0.048 g CD9055 until a homogenous mixture was obtained.

A second oil phase was prepared by mixing 100.89 g of the perfume oil, 100.89 g isopropyl myristate, and 0.22 g 2,2'-azobis(2-methylbutyronitrile) in a jacketed stainless-steel reactor. The reactor was held at 35° C. and the oil solution mixed. A nitrogen blanket was applied to the reactor at a rate of 100 cc/min. The second oil composition was heated to 70° C. in 45 minutes, held at 70° C. for 45 minutes, then cooled to 50° C. in 45 minutes. Once cooled to 50° C. the first oil phase was added, and the combined oils mixed for another 10 minutes at 50° C.

The water phase was then added to the combined oil phase. High shear agitation was then applied to produce an emulsion with volume weighted median size of 36.96 µm, determined via Method 9. The reactor was then mixed with a 3" diameter marine propeller blade, 0.26 g 4,4'-azobis[4-cyanovaleric acid] and 100 g demineralized water added, covered, and the temperature increased to 75° C. in 60 minutes, held at 75° C. for 4 hours, increased to 95° C. in 60 minutes, and held at 95° C. for 6 hours. The batch was cooled to 25° C. in 90 minutes. The percentage of solids was measured at 36.30 wt %.

Sample 11:

A water phase was prepared by mixing 400.50 g demineralized water, 55.50 g of a 5 wt % aqueous solution of Selvol 540, and 2.30 g acetic acid at room temperature. To the above water phase solution, 2.30 g Chitoclear chitosan was added and mixed until it is dissolved. 1.61 g potassium persulfate was then added to the above solution and mixed until it is dissolved.

A first oil phase was prepared by mixing 22.41 g perfume oil, 4.00 g CN975, 0.048 g TBAEMA and 0.048 g CD9055 until a homogenous mixture was obtained.

A second oil phase was prepared by mixing 100.89 g of the perfume oil, 100.89 g isopropyl myristate, and 0.22 g 2,2'-azobis(2-methylbutyronitrile) in a jacketed stainless-steel reactor. The reactor was held at 35° C. and the oil solution mixed. A nitrogen blanket was applied to the reactor at a rate of 100 cc/min. The second oil composition was heated to 70° C. in 45 minutes, held at 70° C. for 45 minutes, then cooled to 50° C. in 45 minutes. Once cooled to 50° C. the first oil phase was added, and the combined oils mixed for another 10 minutes at 50° C.

The water phase was then added to the combined oil phase. High shear agitation was then applied to produce an emulsion with volume weighted median size of 25.37 µm, determined via Method 9. The reactor was then mixed with a 3" diameter marine propeller blade, 0.26 g 4,4'-azobis[4-cyanovaleric acid] and 100 g demineralized water added, covered, and the temperature increased to 75° C. in 60 minutes, held at 75° C. for 4 hours, increased to 95° C. in 60 minutes, and held at 95° C. for 6 hours. The batch was cooled to 25° C. in 90 minutes. The percentage of solids was measured at 35.22 wt %.

Sample 12:

A water phase was prepared by mixing 143.91 g demineralized water, 110.00 g of a 5 wt % aqueous solution of Selvol 540, and 204.44 g 4.5% Chitoclear chitosan solution at room temperature. The Chitoclear chitosan solution was prepared by mixing chitosan in hydrochloric acid solution at 25° C. The above chitosan solution was heated to 85° C. in 60 minutes and then held at 85° C. for 120 minutes before it was then cooled to 25° C. in 90 mins. 1.61 g potassium persulfate was then added to the water phase and mixed until it is dissolved.

A first oil phase was prepared by mixing 22.41 g perfume oil, 3.26 g CN975, 0.039 g TBAEMA and 0.039 g CD9055 until a homogenous mixture was obtained.

A second oil phase was prepared by mixing 100.89 g of the perfume oil, 100.89 g isopropyl myristate, and 0.18 g 2,2'-azobis(2-methylbutyronitrile) in a jacketed stainless-steel reactor. The reactor was held at 35° C. and the oil solution mixed. A nitrogen blanket was applied to the reactor at a rate of 100 cc/min. The second oil composition was heated to 70° C. in 45 minutes, held at 70° C. for 45 minutes, then cooled to 50° C. in 45 minutes. Once cooled to 50° C. the first oil phase was added, and the combined oils mixed for another 10 minutes at 50° C.

The water phase was then added to the combined oil phase. High shear agitation was then applied to produce an emulsion with volume weighted median size of 25.37 µm, determined via Method 9. The reactor was then mixed with a 3" diameter marine propeller blade, 0.21 g 4,4'-azobis[4-cyanovaleric acid] and 100 g demineralized water added, covered, and the temperature increased to 75° C. in 60 minutes, held at 75° C. for 4 hours, increased to 95° C. in 60 minutes, and held at 95° C. for 6 hours. The batch was cooled to 25° C. in 90 minutes. The percentage of solids was measured at 37.06 wt %.

Sample 13:

A water phase was prepared by mixing 344.67 g demineralized water, 110.93 g of a 5 wt % aqueous solution of Selvol 540, and 2.30 g acetic acid at room temperature. To the above water phase solution, 2.30 g Chitoclear chitosan and 146.67 g 4.5% Chitoclear chitosan solution were added and mixed until it is dissolved. The Chitoclear chitosan solution was prepared by mixing chitosan in hydrochloric acid solution at 25° C. The above chitosan solution was heated to 85° C. in 60 minutes and then held at 85° C. for 120 minutes before it was then cooled to 25° C. in 90 mins. 1.61 g potassium persulfate was then added to the above solution and mixed until it is dissolved.

A first oil phase was prepared by mixing 22.41 g perfume oil, 4.00 g CN975, 0.048 g TBAEMA and 0.048 g CD9055 until a homogenous mixture was obtained.

A second oil phase was prepared by mixing 100.89 g of the perfume oil, 100.89 g isopropyl myristate, and 0.22 g 2,2'-azobis(2-methylbutyronitrile) in a jacketed stainless-steel reactor. The reactor was held at 35° C. and the oil solution mixed. A nitrogen blanket was applied to the reactor at a rate of 100 cc/min. The second oil composition was heated to 70° C. in 45 minutes, held at 70° C. for 45 minutes, then cooled to 50° C. in 45 minutes. Once cooled to 50° C. the first oil phase was added, and the combined oils mixed for another 10 minutes at 50° C.

The water phase was then added to the combined oil phase. High shear agitation was then applied to produce an emulsion with volume weighted median size of 28.30 µm, determined via Method 9. The reactor was then mixed with a 3" diameter marine propeller blade, 0.26 g 4,4'-azobis[4-cyanovaleric acid] and 100 g demineralized water added, covered, and the temperature increased to 75° C. in 60 minutes, held at 75° C. for 4 hours, increased to 95° C. in 60 minutes, and held at 95° C. for 6 hours. The batch was cooled to 25° C. in 90 minutes. The percentage of solids was measured at 36.11 wt %.

Sample 14:

A water phase was prepared by mixing 253.83 g demineralized water, 55.50 g of a 5 wt % aqueous solution of Selvol 540, and 2.30 g acetic acid at room temperature. To the above water phase solution, 2.30 g Chitoclear chitosan and 146.67 g 4.5% Chitoclear chitosan solution were added and mixed until it is dissolved. The Chitoclear chitosan solution was prepared by mixing chitosan in hydrochloric acid solution at 25° C. The above chitosan solution was heated to 85° C. in 60 minutes and then held at 85° C. for 120 minutes before it was then cooled to 25° C. in 90 mins. 1.61 g potassium persulfate was then added to the above solution and mixed until it is dissolved.

A first oil phase was prepared by mixing 22.41 g perfume oil, 4.00 g CN975, 0.048 g TBAEMA and 0.048 g CD9055 until a homogenous mixture was obtained.

A second oil phase was prepared by mixing 100.89 g of the perfume oil, 100.89 g isopropyl myristate, and 0.22 g 2,2'-azobis(2-methylbutyronitrile) in a jacketed stainless-steel reactor. The reactor was held at 35° C. and the oil solution mixed. A nitrogen blanket was applied to the reactor at a rate of 100 cc/min. The second oil composition was heated to 70° C. in 45 minutes, held at 70° C. for 45 minutes, then cooled to 50° C. in 45 minutes. Once cooled to 50° C. the first oil phase was added, and the combined oils mixed for another 10 minutes at 50° C.

The water phase was then added to the combined oil phase. High shear agitation was then applied to produce an emulsion with volume weighted median size of 32.34 µm, determined via Method 9. The reactor was then mixed with a 3" diameter marine propeller blade, 0.26 g 4,4'-azobis[4-cyanovaleric acid] and 100 g demineralized water added, covered, and the temperature increased to 75° C. in 60 minutes, held at 75° C. for 4 hours, increased to 95° C. in 60 minutes, and held at 95° C. for 6 hours. The batch was cooled to 25° C. in 90 minutes. The percentage of solids was measured at 35.15 wt %.

Sample 15:

A water phase was prepared by mixing 400.50 g demineralized water, 55.50 g of a 5 wt % aqueous solution of Selvol 540, and 2.30 g acetic acid at room temperature. To the above water phase solution, 2.30 g Chitoclear chitosan was added and mixed until it is dissolved. 1.61 g potassium persulfate was then added to the above solution at 35° C. and then heated to 70° C. in 30 minutes. The above water phase was then hold at 70° C. for 60 minutes before it was cooled down to 50° C. in 30 minutes.

A first oil phase was prepared by mixing 22.41 g perfume oil, 4.00 g CN975, 0.048 g TBAEMA and 0.048 g CD9055 until a homogenous mixture was obtained.

A second oil phase was prepared by mixing 100.89 g of the perfume oil, 100.89 g isopropyl myristate, and 0.22 g 2,2'-azobis(2-methylbutyronitrile) in a jacketed stainless-steel reactor. The reactor was held at 35° C. and the oil solution mixed. A nitrogen blanket was applied to the reactor at a rate of 100 cc/min. The second oil composition was heated to 70° C. in 45 minutes, held at 70° C. for 45 minutes, then cooled to 50° C. in 45 minutes. Once cooled to 50° C. the first oil phase was added, and the combined oils mixed for another 10 minutes at 50° C.

The water phase was then added to the combined oil phase. High shear agitation was then applied to produce an emulsion with volume weighted median size of 27.28 µm, determined via Method 9. The reactor was then mixed with a 3" diameter marine propeller blade, 0.26 g 4,4'-azobis[4-cyanovaleric acid] and 100 g demineralized water added, covered, and the temperature increased to 75° C. in 60 minutes, held at 75° C. for 4 hours, increased to 95° C. in 60 minutes, and held at 95° C. for 6 hours. The batch was cooled to 25° C. in 90 minutes. The percentage of solids was measured at 32.77 wt %. The leakage of the slurry is 16.76% which is measured according to method 8.

Example 2: Fragrance Oil Delivery Particles Comprising Chitosan Covalently Bounded to the Polyacrylic Wall Material Sample 16:

A water phase is prepared by mixing 253.91 g demineralized water, and 204.44 g 4.5% Chitoclear chitosan solution at room temperature. The Chitoclear chitosan solution is prepared by mixing chitosan in hydrochloric acid solution at 25° C. The above chitosan solution is heated to 85° C. in 60 minutes and then held at 85° C. for 120 minutes before it is then cooled to 25° C. in 90 mins. 1.61 g potassium persulfate is then added to the water phase and mixed until it is dissolved.

A first oil phase is prepared by mixing 22.41 g perfume oil, 3.26 g CN975, 0.039 g TBAEMA and 0.039 g CD9055 until a homogenous mixture is obtained.

A second oil phase is prepared by mixing 100.89 g of the perfume oil, 100.89 g isopropyl myristate, and 0.18 g 2,2'-azobis(2-methylbutyronitrile) in a jacketed stainless-steel reactor. The reactor is held at 35° C. and the oil solution is mixed. A nitrogen blanket is applied to the reactor at a rate of 100 cc/min. The second oil composition is heated to 70° C. in 45 minutes, hold at 70° C. for 45 minutes, then cooled to 50° C. in 45 minutes. Once cools to 50° C. the first oil phase is added, and the combined oils mix for another 10 minutes at 50° C.

The water phase is then added to the combined oil phase. High shear agitation is then applied to produce an emulsion with target median particle size. The reactor is then mixed with a 3" diameter marine propeller blade, 0.21 g 4,4'-azobis[4-cyanovaleric acid] and 100 g demineralized water are added, covered, and the temperature increases to 75° C. in 60 minutes, hold at 75° C. for 4 hours, increases to 95° C. in 60 minutes, and hold at 95° C. for 6 hours. The batch is then cooled to 25° C. in 90 minutes.

Sample 17:

A water phase is prepared by mixing 309.33 g demineralized water, and 2.30 g acetic acid at room temperature. To the above water phase solution, 2.30 g Chitoclear chitosan and 146.67 g 4.5% Chitoclear chitosan solution are added and mixed until it is dissolved. The Chitoclear chitosan solution is prepared by mixing chitosan in hydrochloric acid solution at 25° C. The above chitosan solution is heated to 85° C. in 60 minutes and then hold at 85° C. for 120 minutes before it is then cooled to 25° C. in 90 mins. 1.61 g potassium persulfate is then added to the above solution and mixes until it is dissolved.

A first oil phase is prepared by mixing 22.41 g perfume oil, 3.26 g CN975, 0.039 g TBAEMA and 0.039 g CD9055 until a homogenous mixture is obtained.

A second oil phase is prepared by mixing 100.89 g of the perfume oil, 100.89 g isopropyl myristate, and 0.18 g 2,2'-azobis(2-methylbutyronitrile) in a jacketed stainless-steel reactor. The reactor is held at 35° C. and the oil solution is mixed. A nitrogen blanket is applied to the reactor at a rate of 100 cc/min. The second oil composition is heated to 70° C. in 45 minutes, hold at 70° C. for 45 minutes, then cooled to 50° C. in 45 minutes. Once cools to 50° C. the first oil phase is added, and the combined oils mix for another 10 minutes at 50° C.

The water phase is then added to the combined oil phase. High shear agitation is then applied to produce an emulsion with target median particle size. The reactor is then mixed with a 3" diameter marine propeller blade, 0.21 g 4,4'-azobis[4-cyanovaleric acid] and 100 g demineralized water are added, covered, and the temperature increases to 75° C. in 60 minutes, hold at 75° C. for 4 hours, increases to 95° C. in 60 minutes, and hold at 95° C. for 6 hours. The batch is then cooled to 25° C. in 90 minutes.

Sample 18:

A first composition was prepared in a 300 mL beaker mixing 78.3 g of fragrance oil, 0.11 g of 2-carboxylethyl acrylate (Merck), 2.25 g CN975—hexafunctional aromatic urethane acrylate oligomer—(Sartomer), 0.2 g 2,2-azobis(2,4-dimethylvaleronitrile) (Chemours) and 0.05 g 2,2-azobis(2-methylbutyronitrile) (Chemours) at 25° C. via magnetic stirring. Then, 39.11 g of isopropyl myristate (BASF) was added to the solution at 25° C. and mixed for 15 minutes with a magnetic stirrer till a homogeneous composition was obtained.

A second composition was prepared comprising 174.2 g of a 2 wt % Chitosan, Chitoclear (primex) aqueous solution (175.5 g distilled water and 3.6 g Chitosan), 0.9 g acetic acid (0.5 wt %) at 25° C. via magnetic stirring. Once Chitoclear is fully dissolved 0.63 g potassium persulfate initiator was added and mixed via magnetic stirrer at 25° C. until full dissolution.

The first composition was added to the second composition and emulsified using an overhead mixer (such as IKA overhead mixer) at 1300 rpm for 30 minutes with a 90 degrees 4 blades stirrer. Then the emulsion was transferred to a 500 mL coated reactor equipped with reflux condenser and overhead stirrer with anchor type impeller. Mixing was kept at 180 rpm for 14 h with the following temperature ramp: i) temperature was first increased to 60° C. in 15 minutes and held at 60° C. for 45 minutes; ii) temperature was increased to 75° C. in 30 minutes, 0.67 g of 4,4-azobis (4-cyanovaleric acid) (Chemours) was added and the mixture held at 75° C. for 4 hours; iii) temperature was increased to 90° C. in 30 minutes and held at 90° C. for 8 hours. The delivery particle slurry was then cooled to 20° C. and used without further treatment.

Sample 19:

A first composition was prepared in a 300 mL beaker mixing 78.3 g of fragrance oil, 0.11 g of 2-carboxyethyl acrylate (Merck), 2.25 g CN975—hexafunctional aromatic urethane acrylate oligomer—(Sartomer), 0.2 g 2,2-azobis(2, 4-dimethylvaleronitrile) (Chemours) and 0.05 g 2,2-azobis (2-methylbutyronitrile) (Chemours) at 25° C. via magnetic stirring. Then, 39.11 g of isopropyl myristate (BASF) was added to the solution at 25° C. and mixed for 15 minutes with a magnetic stirrer till a homogeneous composition was obtained.

A second composition was prepared comprising 174.2 g of a 2 wt % Chitosan, Chitoclear (primex) aqueous solution (175.5 g distilled water and 3.6 g Chitosan), 0.9 g acetic acid (0.5 wt %) at 25° C. via magnetic stirring. Once Chitoclear is fully dissolved 0.67 g of 4,4-azobis(4-cyanovaleric acid) (Chemours) was added and mixed via magnetic stirrer at 25° C. until full dissolution.

The first composition was added to the second composition and emulsified using an overhead mixer (such as IKA overhead mixer) at 1300 rpm for 30 minutes with a 90 degrees 4 blades stirrer. Then the emulsion was transferred to a 500 mL coated reactor equipped with reflux condenser and overhead stirrer with anchor type impeller. Mixing was kept at 180 rpm for 14 h with the following temperature ramp: i) temperature was first increased to 60° C. in 15 minutes and held at 60° C. for 45 minutes; ii) temperature was increased to 75° C. in 30 minutes, 0.12 g Potassium persulfate initiator was added and the mixture held at 75° C. for 4 hours; iii) temperature was increased to 90° C. in 30 minutes and held at 90° C. for 8 hours. The delivery particle slurry was then cooled to 20° C. and used without further treatment.

Sample 20-22:

A first composition was prepared in a 300 mL beaker mixing 78.3 g of fragrance oil, 0.11 g of 2-carboxyethyl acrylate (Merck), 2.25 g CN975—hexafunctional aromatic urethane acrylate oligomer—(Sartomer), 0.2 g 2,2-azobis(2, 4-dimethylvaleronitrile) (Chemours) and 0.05 g 2,2-azobis (2-methylbutyronitrile) (Chemours) at 25° C. via magnetic stirring. Then, 39.11 g of isopropyl myristate (BASF) was added to the solution at 25° C. and mixed for 15 minutes with a magnetic stirrer till a homogeneous composition was obtained.

A second composition was prepared comprising aqueous solution of distilled water, Chitoclear (primex) and 0.9 g acetic acid (0.5 wt %) at 25° C. via magnetic stirring. Once Chitoclear is fully dissolved 0.67 g of 4,4-azobis(4-cyanovaleric acid) (Chemours) was added and mixed until fully dissolved by mixing via Ultra-turrax at 25° C. Once 4,4-azobis(4-cyanovaleric acid) (Chemours) was fully dissolved, the Aerosil R 816 (Evonik) was added and dissolved by mixing via Ultra-turrax at 25° C., as shown in samples 20 to 22 in Table 2 below.

The first composition was added to the second composition and emulsified using an overhead mixer (such as IKA overhead mixer) at 1250 rpm for 30 minutes with a 90 degrees 4 blades stirrer. Then the emulsion was transferred to a 500 mL coated reactor equipped with reflux condenser and overhead stirrer with anchor type impeller. Mixing was kept at 180 rpm for 14 h with the following temperature ramp: i) temperature was first increased to 60° C. in 15 minutes and held at 60° C. for 45 minutes; ii) temperature was increased to 75° C. in 30 minutes, 0.24 g potassium persulfate initiator was added and the mixture held at 75° C. for 4 hours; iii) temperature was increased to 90° C. in 30 minutes and held at 90° C. for 8 hours. The delivery particle slurry was then cooled to 20° C. and used without further treatment.

TABLE 2

| Sample | % chitosan in water solution | % Aerosil R 816 in water solution |
|---|---|---|
| 20 | 1 | 0.5 |
| 21 | 1.5 | 0.5 |
| 22 | 1 | 1 |

Example 3: Liquid Fabric Softener Comprising Delivery Particles

Liquid Fabric Softener comprising Delivery Particles was prepared as described below, and the Delivery Particles tested for leakage, as described in the TEST METHODS Section, as shown in TABLE 3.

A fabric softener composition was prepared according to WO2018/170356. The fabric softener composition was finished by adding the delivery particle slurry using an IKA Ultra Turrax (dispersing element 8G) operated at 10 000 rpm for 1 minute, as shown below in TABLE 3.

TABLE 3

| | Sample 2A | Sample 16A | Sample 7A | Sample 8A |
|---|---|---|---|---|
| | Weight % | | | |
| Deionized water | To balance | To balance | To balance | To balance |
| NaHEDP | 0.007 | 0.007 | 0.007 | 0.007 |
| Formic acid | 0.045 | 0.045 | 0.045 | 0.045 |
| HCl | 0.001 | 0.001 | 0.001 | 0.001 |
| Preservative[a] | 0.023 | 0.023 | 0.023 | 0.023 |
| FSA[b] | 9.19 | 5 | 11 | 9.19 |
| Antifoam[c] | 0.101 | 0.101 | 0.101 | 0.101 |
| Coconut oil | 0.31 | 0.31 | 0.31 | |
| Isopropanol | 0.94 | 0.8 | 0.94 | 0.94 |
| CaCl$_2$ | 0.008 | 0.008 | 0.008 | 0.008 |
| Perfume | 0.4 | | | |
| Perfume via delivery particles from Sample 2 | 0.25 | | | |
| Perfume via delivery particles from Sample 16 | | 0.4 | | |
| Perfume via delivery particles from Sample 7 | | | 0.4 | |
| Perfume via delivery particles from Sample 8 | | | | 0.4 |
| Cationic polymer[d] | 0.3 | 0.3 | 0.3 | 0.3 |
| Leakage (Method 5) | | | | 30% |

[a]Proxel GXL, 20% aqueous dipropylene glycol solution of 1,2-benzisothiazolin-3-one, supplied by Lonza. This material is part of the dispersion that is made and is not added at another point in the process.
[b]DEEDMAC: diethyl-ester-dimethyl-ammonium-chloride
[c]MP10 ®, supplied by Dow Corning, 8% activity
[d]Rheovis ® CDE, cationic polymeric acrylate thickener supplied by BASF TABLE 3 demonstrates a liquid fabric softener composition comprising biodegradable delivery particles with low leakage.

Example 4: Liquid Laundry Detergent Comprising Delivery Particles

Liquid Laundry Detergent Compositions comprising the Delivery Particles were prepared and the Delivery Particles tested for leakage, as described in the TEST METHODS Section, and shown in TABLES 4 below.

TABLE 4

| Ingredient: | Sample 9B | Sample 10B | Sample 11B | Sample 12B % wt | Sample 13B | Sample 14B | Sample 15B |
|---|---|---|---|---|---|---|---|
| C12-45 alkyl-7-ethoxylated | | | | 2.34 | | | |
| C12-14 alkyl-7-ethoxylated | | | | 0.2 | | | |
| Monoethanolamine: | | | | 0.5 | | | |
| $C_{12-14}$ EO•3•$SO_3H$ | | | | | | | |
| Linear alkyl benzene sulfonic acid | | | | 4 | | | |
| sodium hydroxide | | | | 1.9 | | | |
| sodium cumene sulfonate | | | | 0.18 | | | |
| citric acid | | | | 1.4 | | | |
| C12-18 Fatty acid | | | | 1.1 | | | |
| Solvents (1,2-Propanediol, Ethanol) | | | | 1.1 | | | |
| Chelants | | | | 0.2 | | | |
| Soil suspending alkoxylated polyalkylenimine polymer$^a$ | | | | 0.68 | | | |
| Minors (stabilizers, preservatives . . . ) | | | | 1 | | | |
| Hydrogenated castor oil | | | | 0.2 | | | |
| Perfume via delivery particles from Sample 9 | 0.5 | | | | | | |
| Perfume via delivery particles from Sample 10 | | 0.5 | | | | | |
| Perfume via delivery particles from Sample 11 | | | 0.5 | | | | |
| Perfume via delivery particles from Sample 12 | | | | 0.5 | | | |
| Perfume via delivery particles from Sample 13 | | | | | 0.5 | | |
| Perfume via delivery particles from Sample 14 | | | | | | 0.5 | |
| Perfume via delivery particles from Sample 15 | | | | | | | 0.5 |
| water | | | | up to 100 | | | |
| % Leakage | 20.09 | 10.27 | 12.84 | 19.77 | 17.87 | 14.42 | 32.77 |

$^a$600 g/mol molecular weight polyethylenimine core with 24 ethoxylate groups per —NH and 16 propoxylate groups per —NH. Available from BASF (Ludwigshafen, Germany)

TABLE 4 demonstrates a liquid laundry detergent composition comprising biodegradable delivery particles with low leakage.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product composition comprising a treatment adjunct and a population of delivery particles, wherein a delivery particle comprises a core and a wall encapsulating said core, wherein:
   the core comprises a benefit agent and a partitioning modifier;
   the wall is a polymer formed by a radical polymerization reaction between:
   a) a water-soluble polysaccharide comprising at least one amine group;

b) at least one of a multifunctional (meth) acrylate monomer or oligomer;
c) at least one water-soluble thermal free radical initiator;
d) at least one oil soluble thermal free radical initiator;
   wherein at least one of the water-soluble initiators is a persulfate and the water-soluble polysaccharide forms carbon/carbon, oxygen/carbon, and/or nitrogen/carbon bonds with the multifunctional (meth) acrylate monomer and/or oligomer, and with the proviso that the polysaccharide is not an amine ester modified starch;
   wherein the polymer has a biodegradability in 60 days following OECD 301B test above 30% $CO_2$; and
   wherein the delivery particle has a leakage of below 50%, as determined by the Leakage Test described in the TEST METHODS Section.

2. The consumer product composition of claim 1, wherein the radical polymerization reaction further includes:
   e) a mono-and/or di-functional monomer and/or oligomer.

3. The consumer product composition of claim 1, wherein the partitioning modifier is at least one of isopropyl myristate, vegetable oil, modified vegetable oil, mono-, di-, and tri-esters of $C_4$-$C_{24}$ fatty acids, dodecanophenone, lauryl laurate, methyl behenate, methyl laurate, methyl palmitate, methyl stearate, or mixtures thereof.

4. The consumer product composition of claim 1, wherein the water-soluble polysaccharide comprises at least one primary amine.

5. The consumer product composition of claim 1, wherein the water-soluble polysaccharide further comprises hydroxyl moieties.

6. The consumer product composition of claim 1, wherein the wall further comprises a polymer comprising hydroxyl moieties.

7. The consumer product composition of claim 6, wherein the polymer comprising hydroxyl moieties is at least one of pectin, carrageenan, cellulose, xanthan gum, tara gum, konjac gum, alginate, hyaluronic acid, amylose, lignin, diutan gum, gelatin, poly (vinyl alcohol) or mixtures thereof.

8. The consumer product composition of claim 1, wherein the water-soluble polysaccharide is at least 2 weight percentage of the total wall.

9. The consumer product composition of claim 7, wherein the polymer is at least 10 weight percentage of the total wall.

10. The consumer product composition of claim 1, wherein at least one of the water-soluble polysaccharide or the polymer has a molecular weight from 30kDa to 500kDa.

11. The consumer product composition of claim 1, wherein at least one of the multifunctional (meth) acrylate monomer or oligomer is at least one of tri-functional (meth) acrylate, tetra-functional (meth) acrylate, penta-functional (meth) acrylate, hexa-functional (meth) acrylate, hepta-functional (meth) acrylate, or mixtures thereof.

12. The consumer product composition of claim 1, wherein at least one of the multifunctional (meth) acrylate monomer or oligomer comprises a hexafunctional aromatic urethane acrylate.

13. The consumer product composition of claim 1, wherein at least one of the multifunctional (meth) acrylate monomer or oligomer comprises a multifunctional aliphatic urethane acrylate.

14. The consumer product composition of claim 1, wherein at least one of the multifunctional (meth) acrylate monomer or oligomer is at least 5 weight percentage of the total wall.

15. The consumer product composition of claim 1, wherein at least one of the mono-functional monomer, di-functional monomer, or oligomer is independently at least one of:

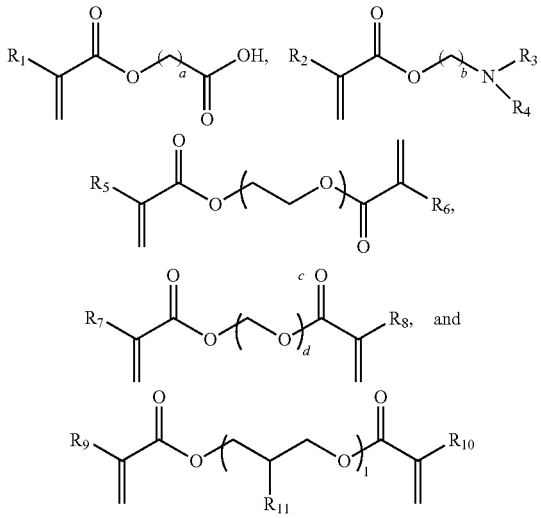

wherein
$R_1$, $R_2$, $R_5$, $R_6$, $R_7$, $R_8$, $R_9$ and $R_{10}$ are independently selected from the group consisting of a hydrogen (*—H) and a methyl group (*—$CH_3$);
a, b, c and d are integers independently selected from 1 to 10,
$R_3$ and $R_4$ are independently selected from the group consisting of

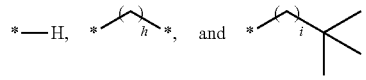

h and i are integers independently selected from 0 to 10;
$R_{11}$ is selected from the group consisting of hydroxyl (*—OH), hydrogen (*—H), and methyl group (*-$CH_3$).

16. The consumer product composition of claim 1, wherein the water-soluble thermal free radical initiator is at least one of ammonium persulfate, potassium persulfate, sodium persulfate or mixtures thereof.

17. The consumer product composition of claim 1, wherein the oil soluble thermal free radical initiator is an azo-based initiator.

18. The consumer product composition of claim 17, wherein the azo-based initiator s at least one of 2,2'-azobis (isobutylnitrile), 2,2'-azobis(2,4-dimethylpentanenitrile), 2,2'-azobis (2,4-dimethylvaleronitrile), 2,2'-azobis(2-methylpropanenitrile), 2,2'-azobis(2-methylbutyronitrile), 1,1'-azobis (cyclohexanecarbonitrile), 1,1'-azobis(cyanocyclohexane) or mixtures thereof.

19. The consumer product composition of claim 1, wherein at least one of the water-soluble polysaccharide or the polymer is fragmented by the water-soluble initiator prior to form at least one of carbon/carbon, oxygen/carbon, or nitrogen/carbon bonds with at least one of the multifunctional (meth) acrylate monomer or oligomer.

20. The consumer product composition of claim 1, wherein at least one of the water-soluble polysaccharide or polymer forms carbon/carbon bonds with at least one of the multifunctional (meth)acrylate monomer or oligomer.

21. The consumer product composition of claim 1, wherein the delivery particle is prepared at a pH from 3 to 7.

22. The consumer product composition of claim 1, wherein the wall has a biodegradability above 30% $CO_2$ in 60 days following OECD 301B test.

23. The consumer product composition of claim 1, wherein the wall of the delivery particles further comprises a coating material.

24. The consumer product composition of claim 1, wherein the treatment adjunct is at least one of surfactants, conditioning actives, deposition aids, rheology modifiers or structurants, bleach systems, stabilizers, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, silicones, hueing agents, aesthetic dyes, neat perfume, additional perfume delivery systems, structure elasticizing agents, carriers, hydrotropes, processing aids, anti-agglomeration agents, coatings, formaldehyde scavengers, pigments, or mixtures thereof.

* * * * *